US010197552B2

(12) United States Patent
Zeng et al.

(10) Patent No.: US 10,197,552 B2
(45) Date of Patent: Feb. 5, 2019

(54) MONITORING CELL-TO-CELL INTERACTIONS

(71) Applicant: Oakland University, Rochester, MI (US)

(72) Inventors: Xiangqun Zeng, Rochester Hills, MI (US); Gerard Madlambayan, Rochester, MI (US); Liang Tan, Changsha (CN); Bahareh Pezeshkian, Rochester, MI (US); Abdul Rehman, Dhahran (SA)

(73) Assignee: Oakland University, Rochester, MI (US)

( * ) Notice: Subject to any disclaimer, the term of this patent is extended or adjusted under 35 U.S.C. 154(b) by 480 days.

(21) Appl. No.: 14/981,076

(22) Filed: Dec. 28, 2015

(65) Prior Publication Data

US 2016/0202235 A1    Jul. 14, 2016

Related U.S. Application Data

(60) Provisional application No. 62/101,142, filed on Jan. 8, 2015.

(51) Int. Cl.
    *G01N 29/02*    (2006.01)
    *G01N 33/483*   (2006.01)
    (Continued)

(52) U.S. Cl.
    CPC ....... *G01N 33/4833* (2013.01); *G01N 29/022* (2013.01); *G01N 29/036* (2013.01); *G01N 29/42* (2013.01); *G01N 29/4472* (2013.01); *G01N 2291/0228* (2013.01); *G01N 2291/0255* (2013.01); *G01N 2291/0256* (2013.01);
    (Continued)

(58) Field of Classification Search
    None
    See application file for complete search history.

(56) References Cited

U.S. PATENT DOCUMENTS 8,346,482 B2    1/2013    Fernandez

OTHER PUBLICATIONS

Shen et al., Nonlabeled Quartz Crystal Microbalance Biosensor for Baterial Detection Using Carbohydrate and Lectin Recognitions, Analytical Chemistry, vol. 79, No. 6, Mar. 15, 2007, pp. 2312-2319. (Year: 2007).*

(Continued)

*Primary Examiner* — Rebecca L Martinez
(74) *Attorney, Agent, or Firm* — Dierker & Kavanaugh, P.C.

(57) ABSTRACT

In a method for monitoring cell-to-cell interactions, a quartz crystal microbalance surface is exposed to a medium including a first cell. The first cell is exposed to a sample including a suspect cell. The first cell is activated prior to or simultaneously with the first cell exposure. Frequency and motional resistance changes versus time are measured after each of: surface exposure to the medium, first cell activation prior to the exposure to the sample, and first cell exposure to the sample; or after each of: surface exposure to the medium and simultaneous first cell activation and sample exposure. From the frequency and motional resistance changes versus time, any of i) a level of adhesion of the suspect cell to the activated first cell, ii) a type of the suspect cell, iii) a behavior or activity of the suspect cell is determined, or iv) activation of the first cell is determined.

18 Claims, 13 Drawing Sheets

(51) Int. Cl.
  *G01N 29/42* (2006.01)
  *G01N 29/036* (2006.01)
  *G01N 29/44* (2006.01)

(52) U.S. Cl.
  CPC .............. *G01N 2291/02466* (2013.01); *G01N 2291/0426* (2013.01)

(56) References Cited

OTHER PUBLICATIONS

Pan et al., Selective collection and detection of leukemia cells on a magnet-quartz crystal microbalance system using aptamer-conjugated magnetic beads, Biosensors and Bioelectronics, 25, Dec. 2, 2009, pp. 1609-1614. (Year: 2009).*
Tan, et al.; "Real-time monitoring of cell mechanical changes induced by endothelial cell activation and their subsequent binding with leukemic cell lines" Biosensors and Bioelectronics; 2014; vol. 56; pp. 151-158.
Bandey, et al.; "Modeling the responses of thickness-shear mode resonators under various loading conditions"; Analytical Chemistry; 1999; vol. 71; No. 11; pp. 2205-2214.
Pezeshkian, et al.; "Leukemia mediated endothelial cell activation modulates leukemia cell susceptibility to chemotherapy through a positive feedback loop mechanism"; PLOS One; 2013; vol. 8; Issue 4; pp. 1-10.

* cited by examiner

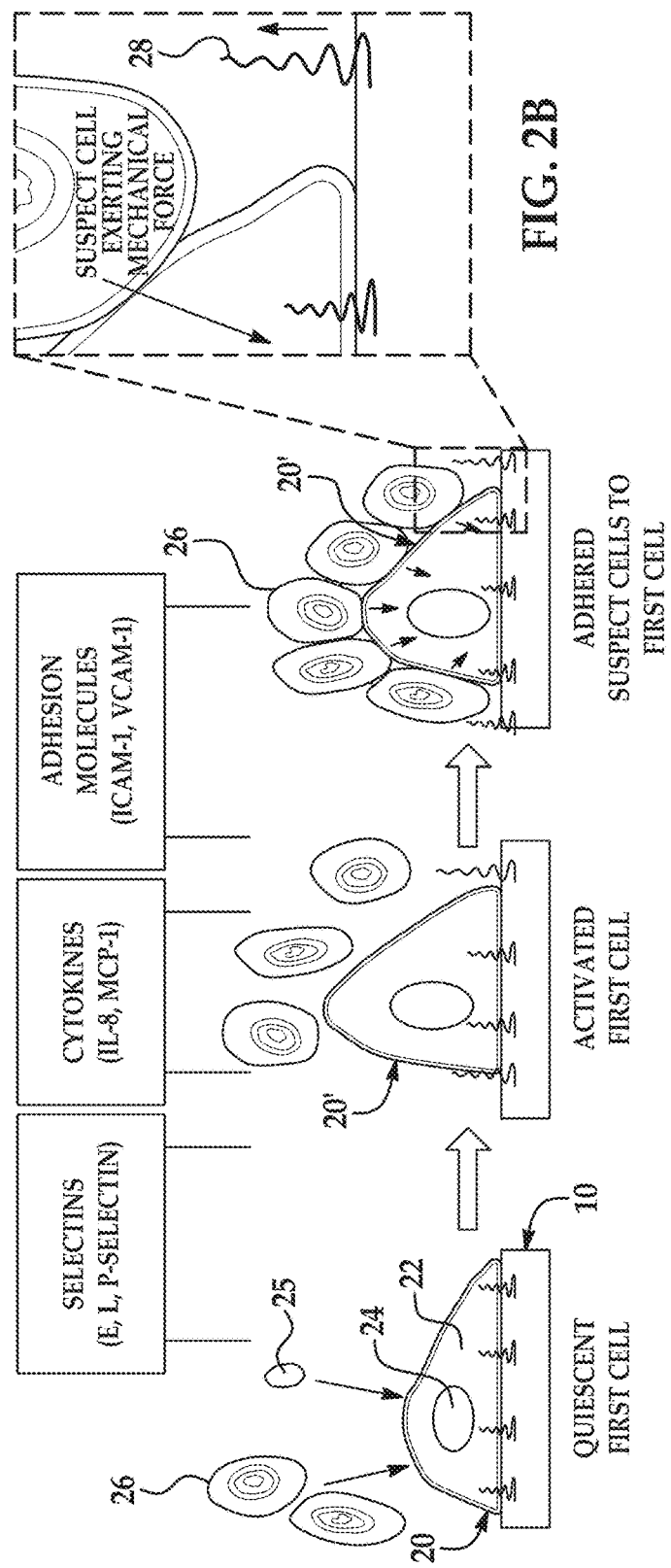

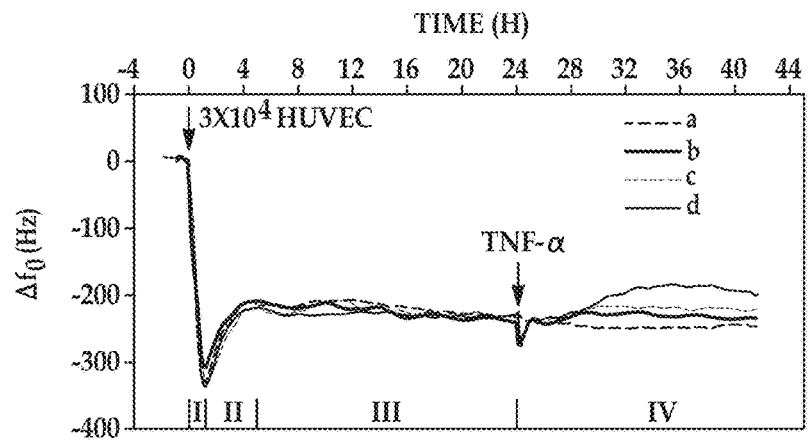
FIG. 3A
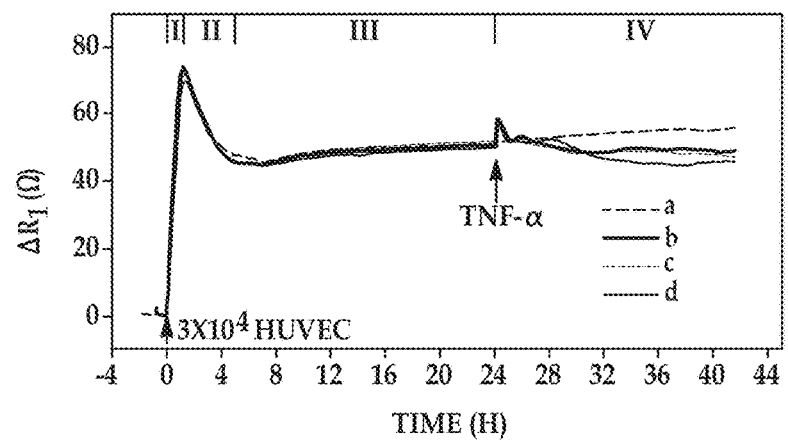
FIG. 3B
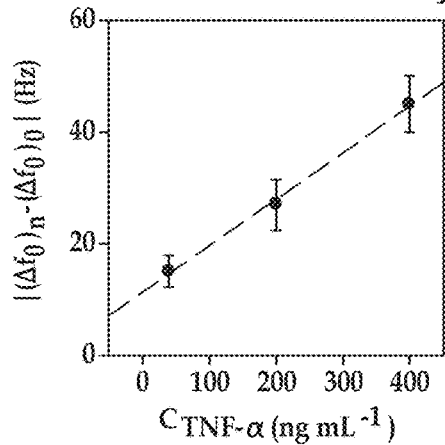 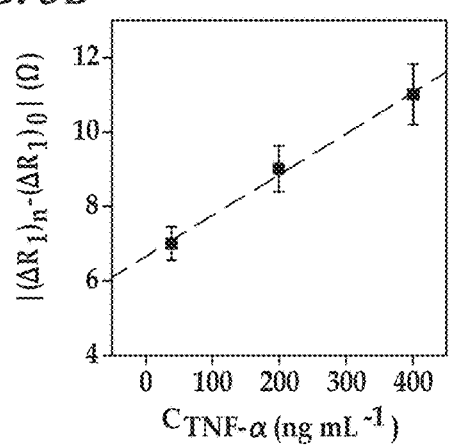
FIG. 3C  FIG. 3D

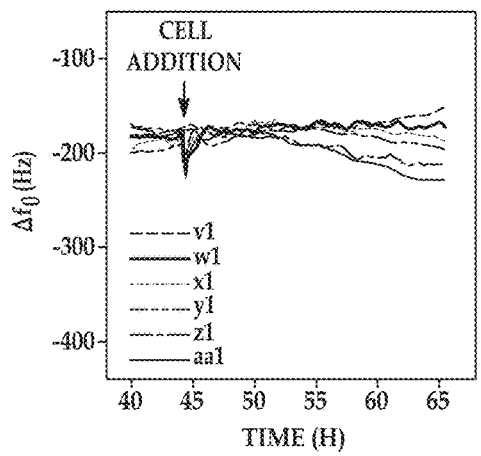
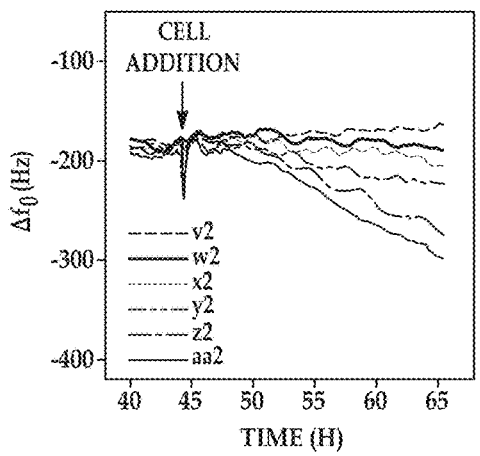
FIG. 13A1　　　　　FIG. 13B1
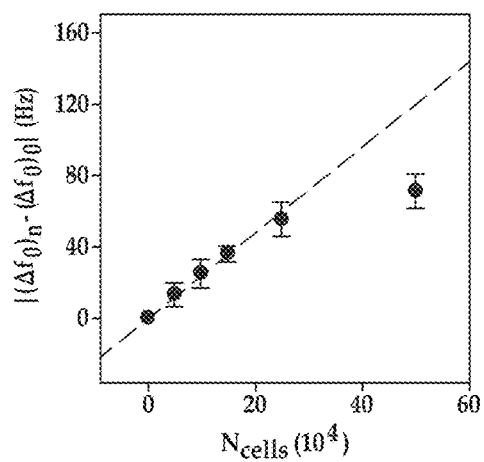
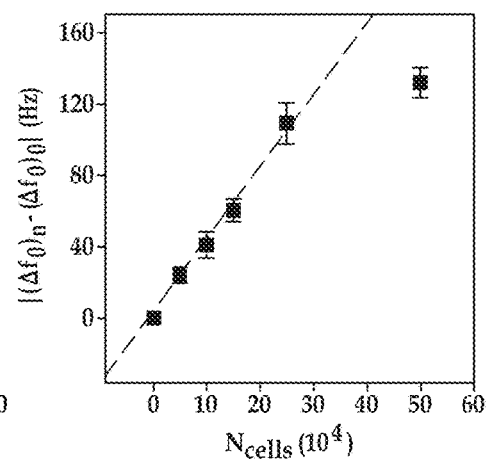
FIG. 13A2　　　　　FIG. 13B2

US 10,197,552 B2

MONITORING CELL-TO-CELL INTERACTIONS

CROSS-REFERENCE TO RELATED APPLICATIONS

This application claims the benefit of U.S. Provisional Application Ser. No. 62/101,142, filed Jan. 8, 2015, which is incorporated by reference herein in its entirety.

STATEMENT REGARDING FEDERALLY SPONSORED RESEARCH OR DEVELOPMENT

This invention was made with government support under Grant No. 1R21EB009513-01A1 by the National Institutes of Health (NIH). The government has certain rights in the invention.

BACKGROUND

Within the human body, different cells may interact with one another. For example, normal blood formation involves interactions between hematopoietic stem cells (HSCs) and extrinsic signals mediated via niches located in the endosteal and vascular regions of the bone marrow. Studying cellular interactions may provide insight with regard to roles that certain cell-to-cell interactions play in the progression, control, etc. of certain diseases. Some cell-to-cell studies involve the immobilization of a first layer of cells, and then the examination of cell changes that occur as a result of a label (e.g., a drug or a toxin) being added to the layer of cells.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 2A is a schematic flow diagram illustrating endothelial cells on a QCM surface before activation, after activation, and after suspect cell exposure, where the inset, labeled FIG. 2B, illustrates the position of the suspect cell with respect to the decaying shear wave;

FIGS. 3A through 3D are plots depicting: the real-time $\Delta f_0$ (i.e., change in frequency) responses to the successive addition of $3 \times 10^4$ human umbilical vein endothelial cells (HUVECs) and tumor necrosis factor-alpha (TNF-$\alpha$) (24 hours later) with different concentrations (FIG. 3A); the real-time $\Delta R_1$ (i.e., change in motional resistance) responses to the successive addition of $3 \times 10^4$ human umbilical vein endothelial cells (HUVECs) and tumor necrosis factor-alpha (TNF-$\alpha$) (24 hours later) with different concentrations (FIG. 3B); $|(\Delta f_0)_n - (\Delta f_0)_0|$ versus the concentration of TNF-$\alpha$ (i.e., $c_{TNF-\alpha}$) (FIG. 3C); and $|(\Delta R_1)_n - (\Delta R_1)_0|$ versus $c_{TNF-\alpha}$ (FIG. 3D); the results are presented as mean±SD (standard deviation, as indicated by the error bar) of triplicate experiments; and the four stages of cell action are shown on the x axis of FIGS. 3A and 3B;

FIGS. 13A1 through 13B2 are plots depicting: the real-time $\Delta f_0$ responses to the addition of HL-60 cells with different concentrations on Au/activated HUVECs (FIG. 13A1); the real-time $\Delta f_0$ responses to the addition of KG-1 cells with different concentrations on Au/activated HUVECs (FIG. 13B1); $|(\Delta f_0)_n - (\Delta f_0)_0|$ versus the number of HL-60 cells (FIG. 13A2); and $|(\Delta f_0)_n - (\Delta f_0)_0|$ versus the number of KG-1 cells (FIG. 13B2); the results are presented as mean±SD (error bar) of triplicate experiments;

DETAILED DESCRIPTION

Figure 1A:
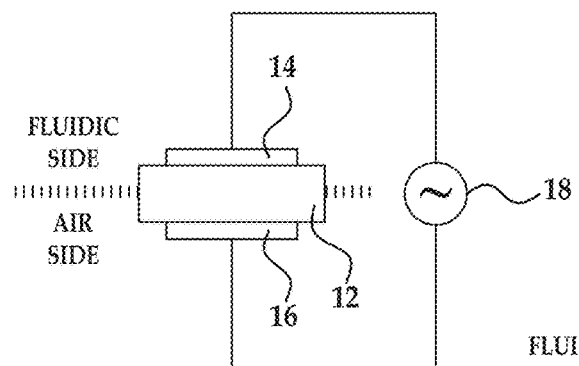
FIG. 1A is a schematic illustration of an example of a quartz crystal microbalance (QCM)

The method disclosed herein enables cell-to-cell interactions to be monitored non-invasively (e.g., no instrument stimulus is used) and without the use of a label (e.g., drugs or toxins). The methods utilize a quartz crystal microbalance (QCM) to monitor frequency and motional resistance changes at several steps. In one example method, frequency and motional resistance changes are monitored at the activation of a first cell and at the interaction between the activated first cell and a suspect cell. In another example method, frequency and motional resistance changes are monitored at the interaction of a first cell and an agent, at the attempted activation of the first cell, and at the interaction of the first cell and the suspect cell. Coupling the QCM results from several steps together can lead to a determination as to the level of adhesion (including a lack thereof) between the first cell and the suspect cell, the type of suspect cell, the behavior or activity of the suspect cell, and/or whether or not the first cell has been activated. The behavior is varied and can include i) the ability of the suspect/sample cell to activate the medium/first cell (e.g., endothelial) cells), ii) the ability of the suspect/sample cell to adhere to the medium/first cell, iii) the ability of the suspect/sample cell to become quiescent (i.e., not proceed through cell cycle) following adhesion, iv) the ability of the suspect/sample cell to resist chemotherapy treatment upon adhesion, v) the ability of the suspect/sample cell to detach from the medium/first cell and re-enter cell cycle (which may contribute to cancer relapse), or combinations thereof. Any of the determinations may be used to identify disease stage, potential for relapse, identify a treatment plan, etc.

While the examples disclosed herein focus on endothelial cells as the first cell and leukemia cells as the suspect cell, it is to be understood that the methods disclosed herein may be used for monitoring any combination of cells that behave in a similar manner. For example, the first cell may be of the type that is capable of interacting with the surface of the QCM, and the suspect cell may be of the type that is capable of interacting with the first cell. Any combination of host cells as the first cell and bacterial cells as the suspect may be used, where the bacterial cell-host cell interactions at the plasma membrane impacts many biological processes (e.g., induces an inflammatory response). Some other example combinations include red blood cells (suspect cell) and endothelial cells (potential to determine if patient has sickled cells, e.g., sickle cell disease), leukocytes/white blood cells (suspect cells) and endothelial cells (potential for detection of: atherosclerosis (e.g., coronary artery disease), thrombosis (the polymorphonuclear leukocyte (PMN) adhesion to the endothelial surface which is important for the thrombosis), inflammatory bowel syndrome, lupus, and other autoimmune disorders), and platelets (suspect cell) and endothelial cells (potential for detection of thrombosis).

In some of the examples disclosed herein, first cell (e.g., endothelial cell (EC)) activation and the subsequent binding of the activated first cell with different suspect cells are monitored in real time. First cell activation and the subsequent intercellular interactions can have significant effects on the regulation of various inflammatory responses and can be causative in generating altered microenvironments that play a role in many biological disorders, such as leukemia and drug induced vascular injuries. It has been found that cell mechanical properties (such as the mechanical consequences during activation and binding) can serve as a functional biomarker of many pathophysiological response mechanisms, diagnostics, biomedical research, etc.

In other examples disclosed herein, first cell binding, exposure of the first cell to an agent, attempted activation of the first cell, and attempted binding of the first cell with different suspect cells are monitored in real time. It has been found that cell mechanical properties (such as the mechanical consequences during first cell binding, agent exposure, attempted activation, and attempted suspect cell binding) can indicate whether the agent used is capable of preventing the activation of the first cell, and subsequently preventing the adhesion of the suspect cell. As an example, the adhesion of leukemia cells to activated endothelial cells protects the leukemia cells from chemotherapy induced apoptosis, and these cells can be causative in the relapse of cancer. By identifying agent(s) that can prevent endothelial cell activation and subsequent leukemia cell binding, potential treatments for leukemia may be identified. For example, a combination treatment using both the identified agent and chemotherapy may be used to eliminate adherent leukemia cells (and thus eliminating leukemia cells that are protected from chemotherapy) and to subsequently kill the leukemia cells.

In the example methods disclosed herein, the QCM is used to monitor the mechanical consequences/changes during first cell attachment to the QCM, agent exposure, activation or attempted activation of the first cell, exposure to suspect cell(s), and/or attachment/detachment of suspect cell(s) to/from first cell(s). The electrical characteristics of the QCM are used to extract the mechanical properties of the cells in contact with the resonator surface. More particularly, the shifts in frequency (f) and motional resistance (R) are related to morphological changes and/or mass change upon cell activation, cell-to-cell interaction, and cell-to-substrate interactions.

QCM is based on the inverse piezoelectric effect in which the application of voltage results in mechanical deformation of the material, for crystalline materials with certain symmetry properties. AT-cut crystals, used in QCM, vibrate in the thickness-shear mode, where two surfaces move in an antiparallel fashion with an exceptionally high quality (Q) factor allowing the deposition of a foreign mass to be detected in sub-nanogram quantities. Besides rigid masses, the sensor is also responsive to changes in the viscoelasticity of an attached film. In aqueous solutions, the QCM displays a damped shear wave penetrating a few hundred nanometers into the bulk solution, and the energy of dissipation can be monitored by impedance spectra or motional resistance changes.

A schematic of the QCM 10 is shown in FIG. 1A. The QCM 10 includes a quartz plate 12 (e.g., an AT-cut crystal) with electrodes 14, 16 formed on opposed sides. In an example, the electrodes 14, 16 are gold electrodes. Any other conductive material may be used for the electrodes 14, 16, including metals, such as copper, platinum, titanium, chromium, etc. Each electrode 14, 16 is attached to QCM electronics 18. Through the electronics 18, an alternating voltage may be applied to the electrodes 14, 16, which causes the quartz plate 12 to vibrate, or oscillate, at a particular frequency.

The electrode 14 that is exposed to a sample (e.g., containing the suspect cell) is the fluidic side of the QCM 10 while the electrode that is exposed to air is the air side of the QCM 10. The electrode 14 is exposed to a medium including the first cell(s), and the first cell(s) adhere to the QCM surface at the electrode 14 to form the attached film (mentioned above). Changes in the attached film, resulting from first cell activation, suspect cell interaction, agent interaction, etc. can be detected by the QCM 10, for example, in the form of shifts in frequency and motional resistance.

Figure 1B:
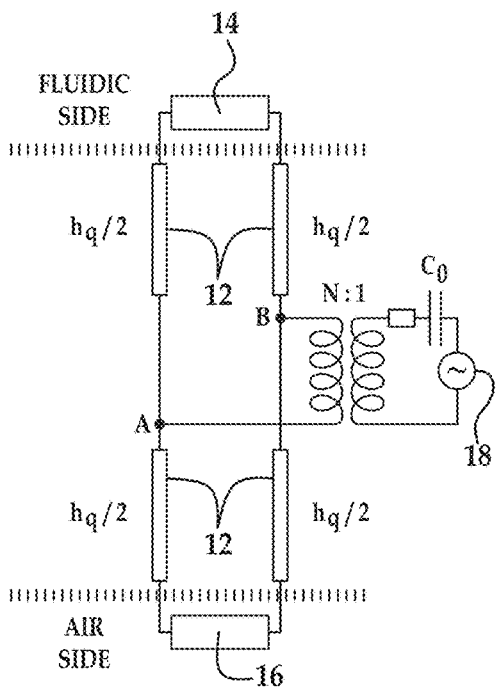
FIG. 1B is a schematic illustration of an example of a Mason circuit model QCM.
Figure 1C:
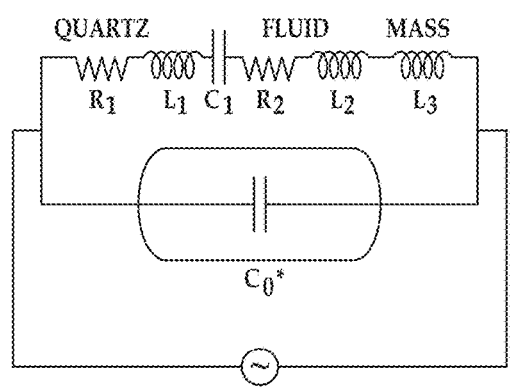
FIG. 1C is a schematic illustration of an example of a Butterworth-van Dyke (BVD) circuit model QCM.

The QCM 10 may be in the form of a Mason circuit model (FIG. 1B) or a Butterworth-van Dyke (BVD) circuit model (FIG. 1C). In the Mason circuit model, there are two acoustic ports that represent the two crystal plates 12. These ports are connected by a transmission line that represents the phase shift and loss experienced by an acoustic wave propagating across the quartz thickness, $h_q$. An N:1 transformer, representing quartz shear displacement (at AB) and the electromechanical coupling between the applied voltage (at 18), couples the acoustic ports to the electrical port. The BVD circuit model includes static and motional arms in parallel. The static arm consists of a capacitance, $C_0^*$, where $C_0^* = C_0 + C_p$ ($C_p$ is the parasitic or stray capacitance, external to the quartz, due to the geometry of the test fixture and electrode pattern). The motional arm, containing $L_1$, $C_1$, and $R_1$, arises due to the electromechanical coupling of piezoelectric quartz. The capacitive component, $C_1$ represents the mechanical elasticity of the system; the inductive component, $L_1$, represents inertial mass; and the resistive component, $R_1$, represents dissipation of energy due to viscous effects, internal friction, and damping from the crystal mounting. The static capacitance, $C_0^*$, dominates the admittance, Y (reciprocal of impedance), away from resonance, while the motional contribution dominates near resonance. $R_2$ represents motional resistance and $L_2$ and $L_3$ represent the motional inductance.

The QCM 10 may be used to relate biophysical changes in cells to the QCM frequency and energy dissipation. However, the decay length of the QCM shear wave is in the nanometer range, making it a surface technique that is generally not able to monitor cell-to-cell interactions which are larger in size (e.g., the size of ECs is several microns). With a suitable ensemble of cells and their microenvironment, a scenario of mass and viscoelastic changes is created, that can be related to the interaction events of different cells. In the method disclosed herein, the first cells alone are used as a response element, both for measuring their own biophysical changes during attempted activation or activation and their interactions with suspect cells and/or other agents (e.g., anti-bodies or other anti-inflammatory compounds). Moreover, these determinations are all made in real-time, and thus are a true representation of what is happening in vivo as the measurements are performed with the whole cell system rather than by analyzing a single biomarker.

In an example of the method, the QCM 10 is exposed to a medium including the first cells 20. As per many physical models, individual cells 20 can be considered as viscoelastic shells (shown as 22 for the first cells 20 in FIG. 2A) around a liquid core (shown as 24 for the first cells 20 in FIG. 2A). When the first cells 20 adhere to the QCM 10 surface, the first cells 20 reconfigure to a relatively flat interface depending upon the mechanical strength and the contact force (see the left most image in FIG. 2A). This results in a change in mechanical energy of the first cell 29.

In an example using a two layer model, an interfacial layer is the effective medium that represents the surface contacting parts of the first cells 20 and has a thickness (h). The whole apical part of the cell 20, whose layer thickness (H) is approximately close to that of the actual cell, is not contributing to the QCM response. But the morphological changes in this part (H) can influence the interfacial layer (h). Thus h<<H and for an acoustically thin film, h<<δ. Here δ is the decay length of the shear wave. Thus, the mechanical properties of the narrow cleft between cell 20 and substrate (QCM 10) can only influence the composite QCM results while the apical cell surface has no impact. Moreover, it is reasonable to assume that only the changes in elastic modulus of the cortex directly contacting the QCM 10 can be seen as QCM response. Although, the overall changes in the area and elastic modulus of the top layer, the variations in cell contacting parameters, and the changes in the osmotic pressure can also influence the character of the interfacial layer.

As such, the mechanical change is dependent upon three factors: 1) the stretching force on the cells 20, 2) the number of adherent cells 20 and the type of binding, and 3) the changes in osmotic pressure due to intake and release of materials. Furthermore, due to the response mechanism of the QCM 10 depending upon the generation of shear transverse waves that decay rapidly within a viscous media such as living cells, the mechanical properties of the narrow cleft between cell 20 and substrate 10 can only influence the composite QCM response while the apical cell surface has no impact (see FIG. 2A). This response can be analyzed by, for example, the Mason circuit model (FIG. 1B), connecting energy loss experienced by an acoustic wave during its propagation to the mass and viscoelastic changes in the contacting medium.

In some examples of the method disclosed herein, the first cells 20 on the surface of the QCM 10 are then activated. In one example, activation is accomplished by exposing the first cell(s) 20 to an activating agent 25 (see FIG. 2A). The activating agent 25 used may vary depending upon the first cell 20 that is used. In an example, the first cell(s) 20 is an endothelial cell and the activating agent 25 is tumor necrosis factor alpha (TNF-α) or interleukin-1 (IL-1). In another example, activation is accomplished simultaneously with the first cell(s) 20 being exposed to a sample containing the suspect cell(s) 26. In this example, the activating agent 25 is produced by the sample (e.g., in response to an external or internal stimuli) when it is exposed to the non-activated first cell(s).

The activation of first cells 20 by external or internal stimuli or by an activating agent 25 results in a morphological change in the first cell 20 and reduces cell 20 contact to the QCM substrate (see the middle image in FIG. 2A, showing activated first cell 20'). This should result in a reduction of stored energy, which should affect the inductance as well as frequency. The frequency of the QCM 10 should increase because of higher oscillation of the QCM 10 due to lesser load on the electrode 14. In addition, the activated first cell 20' contact with the substrate (QCM 10) is less (than prior to activation), and thus the cell bodies lie at larger distances from the QCM electrode 14. Due to surface probing functionality of QCM 10, the generated waves have more penetration power in this scenario, than in a case when the (un-activated) cells 20 are closely aligned. This leads to lesser dissipation of energy and the motional resistance is decreased. In other words, the decay length of the penetrating waves will be higher resulting in a decreased damping of the waves, and decreased motional resistance ($R_1$). Both of these parameters (i.e., frequency and motional resistance) can be quantitatively related to the extent of activation of the first cells 20. As an example, the values of $|(\Delta f_0)_n - (\Delta f_0)_0|$ and $|(R\Delta R_1)_n - (\Delta R_1)_0|$ may be proportional to the activation agent concentration.

When activation is accomplished with an activation agent 25, the method then includes exposing the activated first cells 20' to a sample including the suspect cells 26. When activation occurs simultaneously with exposure to the sample including the suspect cells 26, this additional exposure step is not performed because the suspect cells 26 are already in the presence of the activated first cells 20'.

The sample including the suspect cell 26 may be any medium including a cell that can interact with the activated first cells 20'. As examples, the suspect cells 26 may be leukemia cells, such as HL-60 cells and KG-1 cells, and the medium may be Iscove's Modified Dulbecco's Medium supplemented with fetal bovine serum.

The suspect cells 26 may adhere to the activated first cells 20' (see the right most image in FIG. 2A, but not the inset of FIG. 2B). When suspect cells 26 adhere to activated first cells 20', a reverse of the activation process is initiated. The adherence of suspect cells 26 can exert a mechanical force, which can be considered an additional load within the motional branch of the circuit, which affects the QCM frequency.

The distance of this load from the surface of the oscillator is too far to come into the range of the penetrating wave (see the decaying shear wave 28 in the inset in FIG. 2B), and thus is not detectable. However, the effect of this additional load can deform the underlying activated first cells 20'. This may change the cell 20' contact with the substrate (QCM 10), depending, in part, upon the type and size of the adhering suspect cells 26, their interaction mechanisms to the activated first cells 20', and the number of suspect cells 26 being adhered.

The three boxes showing selectins, cytokines, and adhesion molecules in FIG. 2A are examples of the molecules that can lead to the activation of the first cell 20, which can facilitate the adherence of the suspect cells 26. Additionally, in response to various agents, including tumor necrosis factor (TNF)-$\alpha$ and interleukin (IL)-1$\beta$, endothelial cells become activated, resulting in altered morphology as well as increased expression of various cell adhesion molecules (CAMs) and leukemia supportive cytokines. The CAMs may include E-, L- and P-selectins, VE-cadherin, VCAM-1, ICAM-1, and PECAM-1, and the cytokines may include MCP-1, IL-3, IL-6, and IL-8.

All of the previously described factors bring corresponding changes of frequency and damping resistance of the QCM, which may be used to quantitatively estimate the adherence of the suspect cells. For example, a linear relationship has been observed between net frequency responses derived from leukemia cell binding and known leukemia cell concentrations (e.g., from 0 to $25 \times 10^4$ cells), and thus any unknown leukemia cell concentration can be quantified using the net frequency responses and linear regression fitting. The slope of the line from linear regression fitting represents the sensitivity of the net frequency responses toward the leukemia cell concentration. The linear equation can then be used to determine the leukemia cell concentration in an unknown sample. In particular, the linear fit of the net frequency responses signals versus the leukemia cell concentration may be used to determine the unknown leukemia cell concentration because the signal can be measured. This type of quantification can be performed for other types of suspect cells that exhibit a similar linear relationship between net frequency responses or net motional resistance responses derived from suspect cell binding and known suspect cell concentrations.

The previously described example of the method may also be used to identify an unknown suspect cell. Similar to IR spectra for identifying species, in these instances, the recorded changes of frequency and/or damping resistance of the QCM versus time curves when exposed to the unknown suspect cell may be compared with a library of recorded changes of frequency and/or damping resistance of the QCM versus time curves when exposed to known cells. The type of cell may be identified with the recorded changes for the unknown suspect cell match the data of a known cell. As such, the frequency vs. time and damping resistance vs. time curves are like those IR spectra which can be used as signature to identify the cells.

The data obtained from the previously described example of the method may also be used to determine: whether the suspect/sample cell is capable of activating the medium/first cell, the ability of the suspect/sample cell to adhere to the medium/first cell, the ability of suspect/sample cell to become quiescent (i.e., not proceed through cell cycle) following adhesion, the ability of the suspect/sample cell to resist chemotherapy treatment upon adhesion, or combinations thereof. As one example, differing leukemia cell subtypes may modulate the first cell activation process to varying degrees, which is exhibited by the frequency and/or damping resistance of the QCM. These frequency and/or damping resistance measurements may be correlated with varied chemotherapeutic responses. As another example, the real time QCM data (frequency vs. time and damping resistance vs. time) curves are like the IR spectra. A library of the QCM data (e.g., QCM signatures recorded at various controlled experimental conditions) can be generated, and the data in the library can be used to identify whether the suspect cells become quiescent. For example, if the suspect cells do not attach to the endothelial cells, it may be because the suspect cells do not activate and/or adhere to the endothelial cells. Additionally, the affinity of the binding of the suspect cells with the first cells can be obtained using QCM data at various concentrations. The information can all be pooled together to obtain qualitative and quantitative information.

In the example of the method previously described, the frequency changes and motional resistance changes may be performed in the presence of an agent that affects the level of adhesion of the suspect cell to the first cell or the behavior or activity of the suspect cell. For example, the agent may be a compound that prevents the adhesion of the suspect cell to the first cell, or a compound that induces the release of an already adhered suspect cell.

In one example, the agent is exposed to the QCM 10 after the first cell has been activated (e.g., after exposing the first cell to the activation agent), but prior to exposing the first cell to the sample including the suspect cell. This example may be used to test whether the agent is capable of blocking adhesion of the suspect cells to the activated first cells. The frequency and motional resistance changes may be monitored after the agent is added, and after the suspect cells are added. If the addition of the suspect cells produces no measurable signal changes, it can be concluded that the agent is capable of blocking the adhesion of the particular suspect cells.

In another example, the agent is exposed to the QCM 10 after the first cell has been activated and exposed to the sample including the suspect cell. This example may be used to test whether the agent is capable of inducing the release of suspect cells adhered to the activated first cells. The frequency and motional resistance changes may be monitored after the suspect cells are added, and after the agent is added. If the addition of the agent produces measurable signal changes, it can be concluded that the agent is capable of releasing the adhered suspect cells from the activated first cells. This may be used to test compounds for cancer treatments. In particular, this may be used to rule out those compounds that can induce the detachment of the suspect cells from the first cells, especially when the detached suspect cells can re-enter the cell cycle (which may contribute to cancer relapse).

In another example of the method disclosed herein, the QCM 10 is exposed to the medium including the first cell, and then is exposed to the agent. In these examples, the agent may be any compound that can, or is believed to, prevent the activation of the first cell, and subsequently prevent the adhesion of the suspect cell. Examples of the agent include anti-inflammatory compounds, such as thalidomide and lenalidomide. As such, this example may be used to test whether the agent is capable of preventing first cell activation and preventing adhesion of the suspect cells.

In this example of the method, the agent may first be exposed to sample including the suspect cells (i.e., in a pre-incubation step), and then the incubated sample (including both the agent and the suspect cells) may be exposed to the first cell, with or without additional agent. In another example of this method, the agent and the sample including the suspect cell may be added simultaneously to the first cells without the pre-incubation.

In this example of the method, the suspect cell may be an activation agent of the first cell, and thus attempted activation of the first cell is performed when the first cell is exposed to the sample including the suspect cell.

When the agent is exposed to the first cell simultaneously with the introduction of the sample including the suspect cell, the frequency versus time and motional resistance versus time changes of the QCM 10 may be monitored before and after the agent and suspect cells are simultaneously added (which also occurs simultaneously with attempted activation). If the measurable signal changes match previously recorded frequency versus time and motional resistance versus time changes for the activation and/or binding of the suspect cells, it can be concluded that the agent is not capable of blocking first cell activation and/or the adhesion of the particular suspect cells. However, if there is no measurable signal change or the measurable signal changes do not match previously recorded frequency and motional resistance changes for the activation and/or binding of the suspect cells, it can be concluded that the agent is capable of blocking first cell activation and/or the adhesion of the particular suspect cells. The signal amplitude may also be related to the concentration of the added agent and to the concentration of the suspect cells. Using a library of QCM data, the signal amplitude may be used to obtain information related to various clinical or biomedical research conditions.

In any of the examples of the method disclosed herein, the QCM 10 may be exposed to a blank medium for a predetermined time before exposing the QCM 10 to the medium including the first cell. The blank medium may be the same medium that is used to introduce the first cell, except that no first cells are present in the blank medium. An example of the blank medium is Iscove's Modified Dulbecco's Medium supplemented with fetal bovine serum.

While the QCM 10 is exposed to the blank medium, change(s) in frequency and change(s) in motional resistance are measured. These measurements may be taken continuously or at predetermined intervals (e.g., every minute) to determine when stable baselines for $\Delta f_0$ and $\Delta R_1$ are achieved. The stable baselines indicate that the QCM 10 is equilibrated, and the respective baselines may be used as a resonant frequency baseline value and a motional resistance baseline value in a subsequent quality control step.

The predetermined time that the QCM 10 is exposed to the blank medium depends, in part, on how long it takes for the QCM 10 to equilibrate. In an example, the QCM 10 is exposed to the blank medium for about 2 hours.

A quality control step may be performed after the QCM has been equilibrated and has been exposed to the medium including the first cell. To perform the quality control step, the frequency and motional resistance changes are monitored after the QCM 10 has been exposed to the medium including the first cell. Before exposing the first cell to the sample including the suspect cell and/or to the agent, the frequency change and the motional resistance change signals are allowed to return to the previously determined resonant frequency baseline value and the motional resistance baseline value, respectively. Since the endothelial cell attachment has a unique feature (as shown in the QCM frequency vs. time and damping resistance vs. time curves, stages I and II), these features can be used as a quality control factor to be sure all batches of the first cells are in good quality for further experiments (e.g., to study first cell activation and subsequent attachment with the leukemia cells).

In the examples disclosed herein, the cell-to-cell interactions of the chosen model system can be monitored by a surface technique, rather than by invasive protocols. For complicated systems involving living cells, more sophisticated models based on physical principles of interaction are contemplated herein.

To further illustrate the present disclosure, examples are given herein. It is to be understood that these examples are provided for illustrative purposes and are not to be construed as limiting the scope of the present disclosure.

EXAMPLES

Example 1

Materials and Apparatus

Tumor necrosis factor-alpha (TNF-α) was purchased from HUMANZYME (USA). Phosphate-buffered saline (PBS, 0.1 M, pH 7.4) was purchased from Invitrogen and employed in the electrochemical measurements.

The gold QCM consists of a thin AT-cut quartz crystal wafer with a gold electrode on each side (9 MHz, non-polished with ~1000 Å gold, geometric area is 0.28 cm$^2$, Beijing Chenjing Electronics Co., Ltd., China). The gold QCM was mounted between two biocompatible silicon O-rings to allow only one side of the gold electrode to be exposed to the liquid. The reaction chamber above the crystal was held with a 1 mL chlorinated polyethylene centrifugal tube. The device, being covered, was placed in a humidified $CO_2$ incubator controlled at 5% $CO_2$ and 37° C. to prevent evaporation from the culture holder.

The gold QCM was a lumped-element BVD-based equivalent circuit. Besides the impedance elements of the unperturbed resonator ($C_0$, $R_q$, $C_q$, $L_q$), the particular surface loading was accounted for by an additional resistance $R_{load}$ and an additional inductance $L_{load}$ within the motional branch of the circuit. The experimental data in Example 1 is described in terms of changes of two parameters, i.e., frequency and motional resistance with respect to the values of the same resonator without cell ensembles.

An RQCM instrument (Maxtek Inc., USA) was used to simultaneously record resonant frequency ($f_0$) and motional resistance ($R_1$) of the QCM electrodes.

Cyclic voltammetry (CV) and electrochemical impedance spectroscopy (EIS) experiments were performed with a potentiostat/galvanostat (EG&G Par model 2263) by using a three-electrode electrolytic cell. The QCM gold electrode acted as the working electrode. An Ag/AgCl reference electrode (saturated KCl) served as the reference electrode. A platinum wire served as the counter electrode.

The cell-modality observation was performed using an inverted optical microscope (Nikon TMS-F, Japan) with a digital camera (SPOT, 1600×1200 pixels, Diagnostic Instrument Inc. USA).

Cell Culture and Measurement Procedures

Human umbilical vein endothelial cells (HUVECs) and acute myelogenous leukemia cell (AMLC) lines HL-60 and KG-1 were cultured, and were maintained at 37° C. in a $CO_2$ incubator. HUVECs were cultured in EGM-2 medium (500 mL Endothelial Basal Medium-2/EBM-2 supplemented with EGM-2 Single Quotes: 10 ml FBS, 0.2 ml hydrocortisone, 2 ml hFGF, 0.5 ml VEGF, 0.5 ml IGF-1, 0.5 ml ascorbic acid, 0.5 ml hEGF, 0.5 ml GA-1000, 0.5 ml heparin; Lonza, USA). HL-60 and KG-1 cells were grown in Iscove's Modified Dulbecco's Medium (IMDM, Hyclone, USA) supplemented with 20% fetal bovine serum (FBS, Gibco, USA).

After being sterilized with 75% ethanol under UV light for 0.5 hours, the QCM culture-chamber was washed three times with PBS. Then, 500 μL of EGM-2 medium was added and the entire culture-chamber was put into the incubator. As soon as the QCM readout reached a stable baseline, 50 μL of EGM-2 medium containing freshly trypsinized $3\times10^4$ cells was added. All QCM measurements were performed in a static mode without stirring. The $\Delta f_0$ and $\Delta R_1$ responses were simultaneously monitored in the process of cell attachment and growth in the next 24 hours.

Next, the EGM-2 medium was replaced by a medium containing 10% FBS and TNF-α with a specified concentration (ranging from 0 ng/ml to 400 mg/ml), allowing the HUVECs to suffer growth and activation up to 20 hours. After the concentration of HL-60 and KG-1 cells reached $5\times10^6$ cells $mL^{-1}$, they were collected from the medium by centrifugation at 1500 g for 5 minutes to remove IMDM, and were re-suspended with EGM-2 medium supplemented with 10% FBS. This was performed to reduce variations of the viscosity of the medium for measurements. The density of these suspension cells was determined with a hemacytometer.

Finally, 100 μL of the cell-suspending solution was added into the measuring chamber. The $\Delta f_0$ and $\Delta R_1$ responses were simultaneously monitored for 22 hours.

The gold QCM electrode regeneration was achieved by trypsin proteolysis or trypsinization for 24 hours, followed by washing with piranha solution ($H_2SO_4:H_2O_2$, 7:3) and water in sequence for several times. After being cleaned in this way, the QCM gold electrode could be used repeatedly with good recovery of its initial $f_0$ and $R_1$ values.

Results and Discussion

Adhesion of HUVECs and their Activation by TNF-α

The real time attachment, spreading and growth processes of human umbilical vein endothelial cells (HUVECs) on the QCM gold electrode and the cell responses to the stimulation by TNF-α were investigated. The results are shown in FIGS. 3A and 3B. FIGS. 3A and 3B depict, respectively, the real-time $\Delta f_0$ and $\Delta R_1$ responses to the successive addition of $3\times10^4$ human umbilical vein endothelial cells (HUVECs) and tumor necrosis factor-alpha (TNF-α) with different concentrations. For sample a, the HUCEVs were exposed to no TNF-α (i.e., 0 ng $mL^{-1}$); for sample b, the HUCEVs were exposed to 40 ng $mL^{-1}$ TNF-α; for sample c, the HUCEVs were exposed to 200 ng $mL^{-1}$ TNF-α; and for sample d, the HUCEVs were exposed to 400 ng $mL^{-1}$ TNF-α.

As mentioned herein, animal cells are considered to consist of viscoelastic shells surrounding a liquid core. The shells represent a denser actin cortex and the core represents a relatively fluidic cell interior. Also as mentioned herein, most cells (e.g., diameter≈10 μm to 20 μm) are much larger in size than the characteristic decay length of the QCM shear wave (δ≈0.188 μm for 9 MHz crystal in water). Therefore, the cell layer represents a complex entity, as seen from QCM data interpretation and modeling perspective, where only a small part of cells can be detected by the shear wave. This layer is heterogeneous both laterally along the sensor surface and perpendicular to the sensor surface. Thus, unlike thin rigid films, the signals from the cell require more advanced modeling. With a two layer model (described above), it is assumed that the QCM responses are dominated by viscoelasticity effects, except in the first phase following introduction of cells to the measurement chamber where cells adhere to QCM via gravity forces. Thus, the mass effects are minimal during the activation phase.

Before addition of cells, the QCM was initially equilibrated with the blank growth medium for 2 hours, and stable baselines for $\Delta f_0$ and $\Delta R_1$ were achieved. Equilibration is desirable for several reasons. One reason is the changes of the QCM detection environment. The cell chamber containing the QCM gold electrode was placed in $CO_2$ incubation, in which temperature, pressure, humidity and $CO_2$ concentration were different from those outside the incubator. The environmental changes might result in the shifts of QCM signals. Another reason is the interaction between growth medium and the electrode surface. In this example, EGM-2 medium containing 2% fetal bovine serum and many biomolecules including hFGF, VEGF, IGF-1, ascorbic acid, hEGF, GA-1000 and heparin were employed in the real-time cellular analysis. These proteins and amino acids can be adsorbed and produce a protein-covered layer on the gold electrode surface, which could lead to the changes of QCM signals. The $\Delta f_0$ and $\Delta R_1$ signals attained a baseline after 2 hours, suggesting that the QCM electrode reached a relatively stable stage. The subsequent cell adhesion steps were then performed.

In FIGS. 3A and 3B, overshoot signals could be observed in both the $\Delta f_0$ and $\Delta R_1$ curves after addition of the HUVECs and TNF-α. These are related to the changes of environments in the CO2 incubator from manually operating the incubator door in the process of the sample addition. However, these signals had almost no influence on the final cell analysis because the $\Delta f_0$ and $\Delta R_1$ signals could be recovered to the original baseline in half an hour.

According to the QCM responses shown in FIGS. 3A and 3B, the cell action may essentially be divided into four stages, i.e., Stage I (0-1.2 hours), Stage II (1.2-5.0 hours), Stage III (5.0-24 hours) and Stage IV (24-41 hours). In general, three important phases are included in the generation of cells cultured in vitro: adhesion phase, latent phase and logarithmic growth phase, which are represented by Stages I-III respectively, in the QCM response.

In Stage I, HUVECs underwent sedimentation and reached the electrode surface under the influence of gravity, after they were added into the incubation chamber. Immediately after, these cells could react with some cell adhesive proteins, including fibronectin on the electrode surface, which were initially present in growth medium, and complete the cellular adhesion process. This complicated procedure resulted in the notable decrease of frequency, i.e., ~320 Hz and increase of resistance, i.e., ~70Ω. Subsequently, the trends of $\Delta f_0$ and $\Delta R_1$ were reversed in Stage II, suggesting the advent of the latent phase in which cells changed or rearranged their cytoskeletons. However, both the frequency and resistance shifts were ~30% of what was observed in Stage I. Moreover, the frequency and resistance shifts were coherent to each other in the two stages, which can only be correlated to changes in cytoskeleton and cell contacts to the surface without involving any shrinkage of the cells, reaching a dynamic equilibrium in the end.

In Stage III, the QCM responses suffered minor but continuous frequency and resistance shifts which were opposite to Stage II, depicting the evolution from the latent phase to the logarithmic growth phase. Theoretically, the cell population should be doubled in Stage III (i.e., due to the process of cellular division and proliferation on the QCM gold electrode). The QCM response is highly dependent upon the cell coverage on the electrode and the contact area. It is possible that the contact area of cells on the electrode surface increased to a smaller extent during cell division. Cellular proliferation is a slow process in which cells undergo gradual expansion. In other words, the cell coverage on the electrode surface was increasing at a slower rate. As a result, minor but continuous frequency and resistance shifts, rather than great QCM signal changes, were observed in Stage III.

From FIGS. 3A and 3B, the statistical conclusions regarding the reproducibility of the data can also be drawn. In particular, biological systems show substantial individual deviations between different cells which can result in low reproducibility. However, in this case, there was ~10% deviation for QCM response at Stage I for all the experiments, and that was further reduced to ~5-6% in the subsequent stages, thus making the data very reliable.

The time scale of this technique indicates its possible involvement in rapid screening of such phenomena especially in disease microenvironments, in comparison to biological studies, which may be more specific but may also require tedious procedures and demanding expertise. Unfortunately, most of the biological study methods are time consuming, and may require supportive studies using in vivo transplantation in animal models, which may take many days to be completed and still provide only retrospective analyses with no real-time information. Surface techniques, like Surface Plasmon Resonance (SPR), are usually unable to detect such changes and on the other hand, many cell based electrochemical protocols e.g., Electric cell-substrate impedance sensing (ECIS), are limited only to end point analysis.

The addition of TNF-α at the 24th hour led to different QCM shifts (Stage IV). The $\Delta f_0$ was positive while $\Delta R_1$ was negative, gradually reaching to the plateaus. The extent of these changes was enhanced with increasing TNF-α concentrations, which were ranging from 0 ng ml$^{-1}$ to 400 ng ml$^{-1}$. The increased $\Delta f_0$ and decreased $\Delta R_1$ values in the presence of TNF-α indicate the decline of the cell coverage that should be derived from the activation of HUVECs, leading to the decrease of the contact area between cells and the electrode surface. Moreover, in Stage IV, the frequency shifts were 15% and resistance changes were 7% as compared to those in Stage I, for the maximum reported concentration of TNF-α. This means that shift in resistance value is much smaller than the shift in the frequency value. This smaller shift of the resistance in comparison to the frequency suggests that the contacting film has become more rigid after stimulation by TNF-α. This indicates that, in addition to decreased cell surface contacts, some changes in fluidic cell interior may also occur which can be associated to the expression of cellular adhesion molecules (CAMs). Another possibility is the release of water from the cortex as a result of changes in osmotic pressure due to EC activation, the consequence of which is a more rigid cell layer. Therefore, the frequency changes are larger than the resistance changes.

The subtlety of these changes is detectable only by the QCM technology, with combined analysis of the frequency and motional resistance. The appearance of the signal plateaus after cell activation suggests that the adhered HUVECs retained their activity, instead of being detached from the electrode or being inactive. Here $|(\Delta f_0)_n - (\Delta f_0)_0|$ and $|(\Delta R_1)_n - (\Delta R_1)_0|$ are defined as the changes of $\Delta f_0$ and $\Delta R_1$ signals induced by TNF-α, respectively, where $(\Delta f_0)_0$, $(\Delta R_1)_0$, $(\Delta f_0)_n$ and $(\Delta R_1)_n$ represent the frequency and resistance shifts attributed to cell action in the absence ($(\Delta f_0)_0$ and $(\Delta R_1)_0$) and presence ($(\Delta f_0)$, and $(\Delta R_1)$,) of TNF-α, respectively.

As shown in FIGS. 3C and 3D, the values of $|(\Delta f_0)_n - (\Delta f_0)_0|$ and $|(\Delta R_1)_n - (\Delta R_1)_0|$ were found to be proportional to the TNF-α concentration, which means that TNF-α with high concentration had the greatest influence on the activation of HUVECs, resulting in the shrinkage of the cell adhesion area as well as the expression of adherent molecules to greater extents.

Figure 4A:
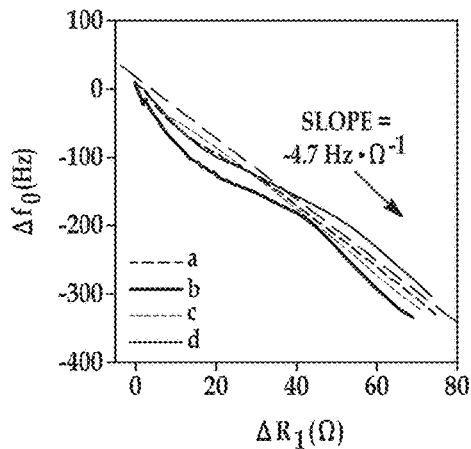
FIGS. 4A through 4D are plots indicating the relationships of $\Delta f_0$ versus $\Delta R_1$ in stage I (FIG. 4A), stage II (FIG. 4B), stage III (FIG. 4C) and stage IV (FIG. 4D) corresponding to quartz crystal microbalance (QCM) responses shown in FIGS. 3A and 3B.
Figure 4B:
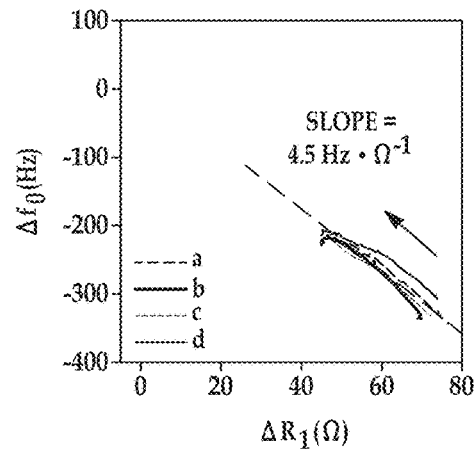
Figure 4C:
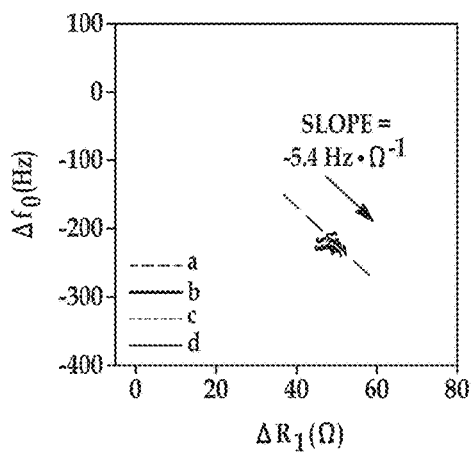
Figure 4D:
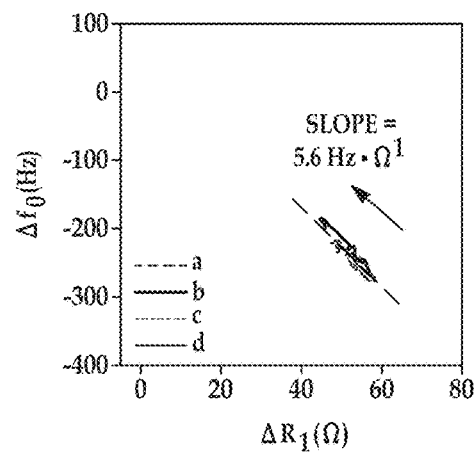

The $\Delta f_0$ and $\Delta R_1$ signals in FIGS. 3A through 3D were analyzed for the QCM response mechanism. FIGS. 4A through 4D show the relationship between $\Delta f_0$ and $\Delta R_1$ for samples a-d in Stages I-IV, respectively. In other words, FIG. 4A shows the relationship between $\Delta f_0$ and $\Delta R_1$ in Stage I, FIG. 4B shows the relationship between $\Delta f_0$ and $\Delta R_1$ in Stage II, FIG. 4C shows the relationship between $\Delta f_0$ and $\Delta R_1$ in Stage III, and FIG. 4D shows the relationship between $\Delta f_0$ and $\Delta R_1$ in Stage IV. In all these events, the $|\Delta f_0/\Delta R_1|$ ratio is smaller than 10 Hz $\Omega^{-1}$, the theoretical threshold value for a 9 MHz QCM crystal for having dominant mass effect. Therefore, all these events can be considered to be controlled by viscoelastic changes. However, this ratio is largest for Stage IV, indicating increased involvement of the mass changes in this stage, as affected by the processes associated with EC activation.

Figure 5A:
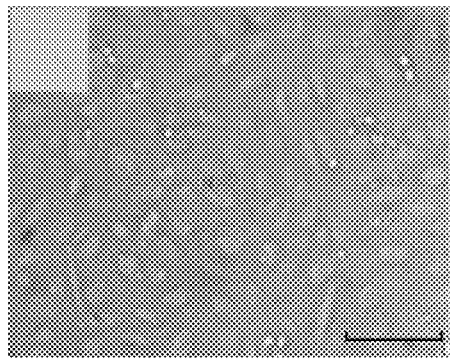
FIGS. 5A through 5D are microscope images of HUVECs taken with a 10× objective in the absence (FIG. 5A) and presence of 40 ng mL$^{-1}$ TNF-$\alpha$ (FIG. 5B), 200 ng mL$^{-1}$ TNF-$\alpha$ (FIG. 5C) and 400 ng mL$^{-1}$ TNF-$\alpha$ (FIG. 5D), where the scale bar represents 50 µm.
Figure 5B:
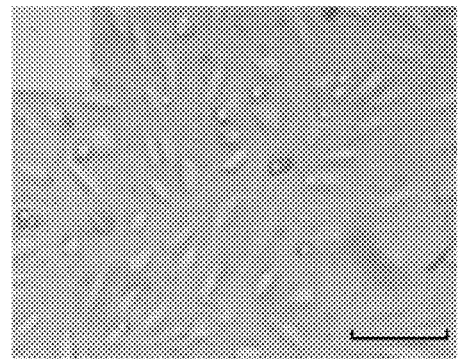
Figure 5C:
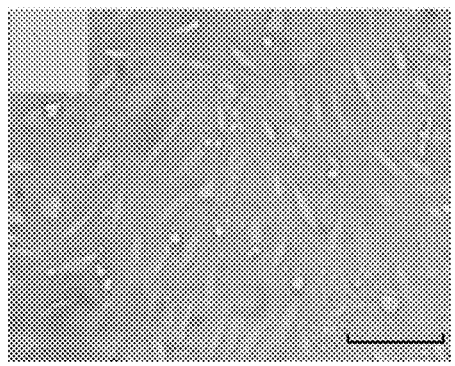
Figure 5D:
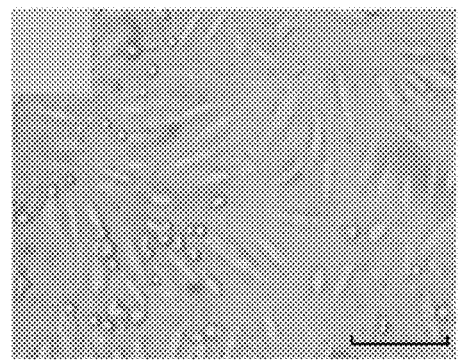

Microscopic images proved the validity of the QCM experimental results. As shown in FIG. 5A, the adhered HUVECs, being closely interconnected, were regular polygons in the absence of TNF-α. The average size of cells was ≈17 µm as described in Countess™ Cell Data Sheet from Invitrogen. After stimulation by TNF-α (FIG. 5B shows cells stimulated with 40 ng mL$^{-1}$ TNF-α, FIG. 5C shows cells stimulated with 200 ng mL$^{-1}$ TNF-α, and FIG. 5D shows cells stimulated with 400 ng mL$^{-1}$ TNF-α), HUVECs gradually became slim and presented shapes resembling small rods with decreased spreading area and increased cell-to-cell separation. The shape-change of cells was more obvious in the presence of TNF-α with high concentration, meaning that TNF-α could effectively induce the activation of HUVECs in a dose dependent manner which. As a result, the shrinking of the cell spreading area would decrease the density and viscosity of the cell layer on the electrode surface, leading to the QCM signals opposite to those in Stage III (curves b-d in FIGS. 3A-3D).

Binding of AML Cells on the Activated Endothelial Cells

Figure 6A:
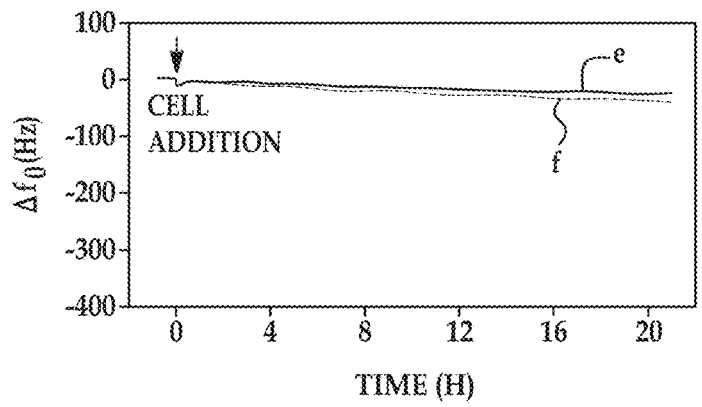
FIGS. 6A and 6B are plots depicting real-time $\Delta f_0$ (FIG. 6A) and $\Delta R_1$ (FIG. 6B) responses to the addition of $25 \times 10^4$ HL-60 cells (e) or $25 \times 10^4$ KG-1 cells (f) on a bare Au electrode of a QCM.
Figure 6B:
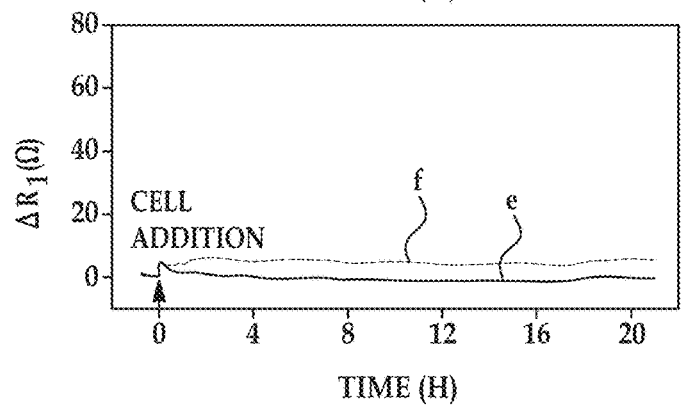

Two AML cell lines, i.e., HL-60 and KG-1 cells, were investigated for their binding with activated ECs, on the QCM gold electrode. The results of control experiments are shown in FIGS. 6A and 6B, where the leukemia cells (i.e., 25×10$^4$ HL-60 cells (e) and 25×10$^4$ KG-1 cells (f)) were directly added to the bare Au QCM electrode. Minor $\Delta f_0$ shifts and almost unchanged $\Delta R_1$, aside from the overshoot signals from the cell addition, were observed after the addition of 25×10$^4$ AML cells. These results indicate that only a few AML cells could be directly adsorbed on the gold electrode, as leukemia cells usually grow in suspension.

Figure 7A:
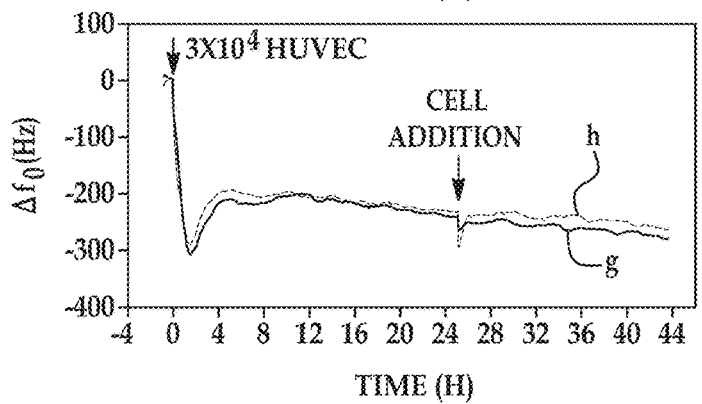
FIGS. 7A and 7B are plots depicting real-time $\Delta f_0$ (FIG. 7A) and $\Delta R_1$ (FIG. 7B) responses to the successive addition of $3 \times 10^4$ HUVECs and $25 \times 10^4$ HL-60 cells (g) or $25 \times 10^4$ KG-1 cells (h) (24 hours later)
Figure 7B:
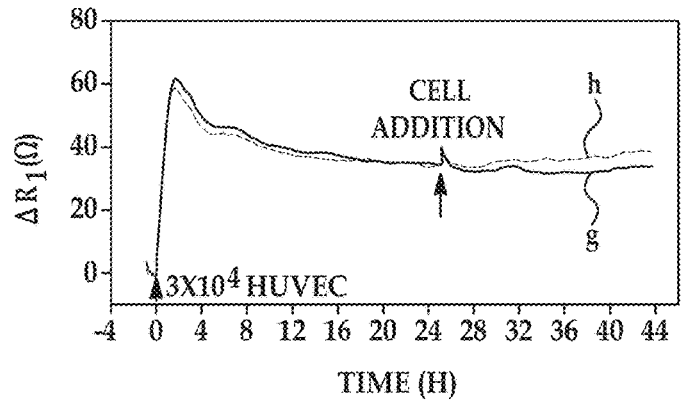

The introduction of AML cells (i.e., $25\times10^4$ HL-60 cells (g) and $25\times10^4$ KG-1 cells (h)) directly onto non-activated HUVECs ($3\times10^4$) attached on the gold electrode did not induce substantial changes in real-time QCM plots as shown in FIGS. 7A and 7B. The $\Delta f_0$ and $\Delta R_1$ shifts attributed to the adhesion and growth of HUVECs retained their initial changing trends in the presence of HL-60 cells (g). With KG-1 cells (h), a slight shift was observed, suggesting that AML cells, especially KG-1, have the ability to activate ECs.

Figure 8A:
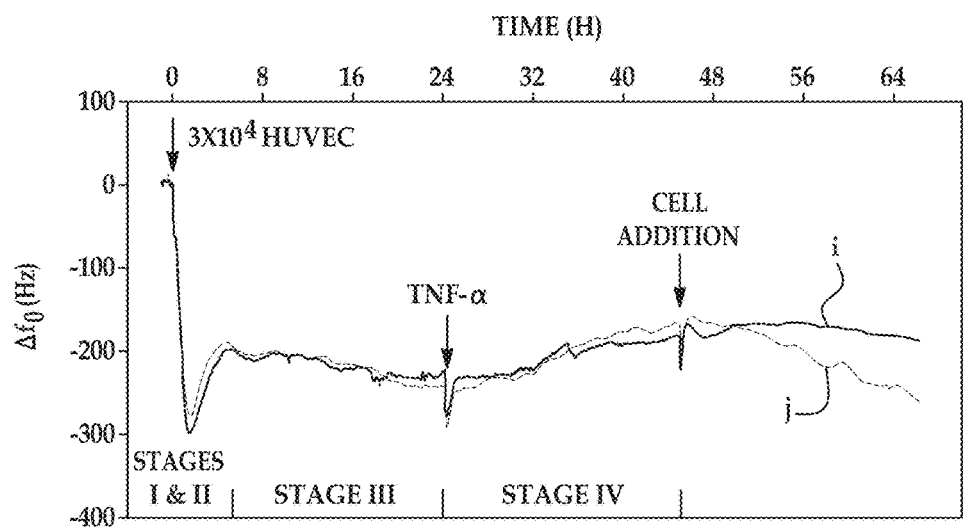
FIGS. 8A and 8B are plots depicting real-time $\Delta f_0$ (FIG. 8A) and $\Delta R_1$ (FIG. 8B) responses to the successive addition of $3 \times 10^4$ HUVECs, 200 ng mL$^{-1}$ TNF-$\alpha$ (24 hours later) and $25 \times 10^4$ HL-60 cells (i) or $25 \times 10^4$ KG-1 cells (j) (45 hours later)
Figure 8B:
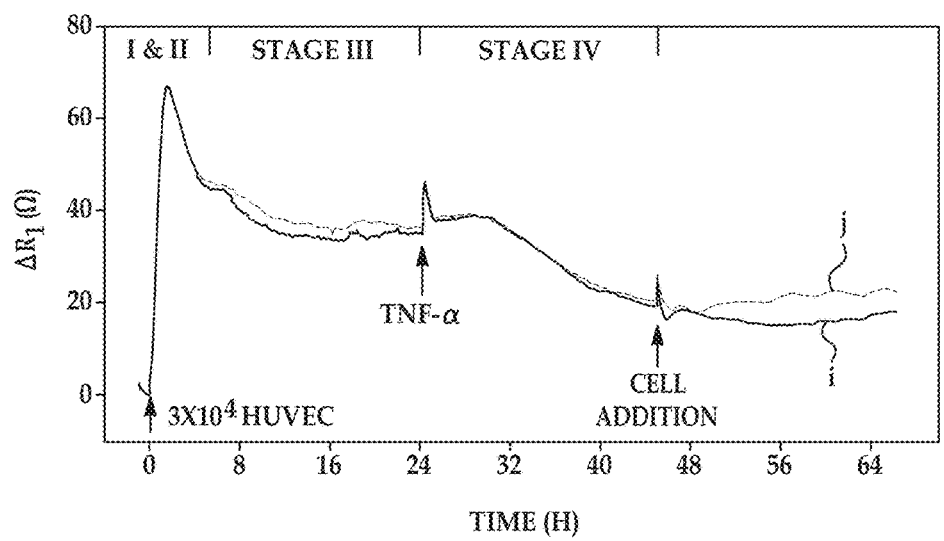

QCM measurements were performed on HUVECs ($3\times10^4$) that were previously activated by TNF-α (200 nm mL$^{-1}$) and that were exposed to the AML cells (i.e., $25\times10^4$ HL-60 cells (i) and $25\times10^4$ KG-1 cells (j)) at the 45$^{th}$ hour. These results are shown in FIGS. 8A and 8B. Parallel experiments were conducted for a minimum of 3 times, and the results including the changing trends and the data values of the QCM responses were well reproduced (RSD<6% for the final $\Delta f_0$ and $\Delta R_1$ responses for identical electrodes). These studies demonstrate the efficacy of the model system and to test that biosensor sensitivity may be linked to the kinetics of EC activation. Here, the whole QCM responses can be divided into three stages. The $\Delta f_0$ and $\Delta R_1$ changes in Stages I and II were derived from the adhesion, growth and activation of HUVECs. The data showed high reproducibility for the experiments. In Stage III, the addition of AML cells gave some interesting signals. One can find the decreased $\Delta f_0$ and increased $\Delta R_1$ shifts (−19.5 Hz and 1.5Ω for HL-60 cells (i); −100 Hz and 4Ω for KG-1 cells (j)) based on a comparison between the QCM responses at the 44th hour and those at the 66th hour. The changing degree of the QCM signals in the presence of KG-1 cells was larger than that in the presence of HL-60 cells. It has been reported that the activation of endothelial cells induced by some activators such as TNF-α and IL-1β can upregulate the expression of CAMs, including E-selectin, ICAM-1, and VCAM-1 on cells. The QCM experimental results indicate that there were intensive interactions between AML cells and HUVECs that were previously activated by TNF-α. These interactions were markedly higher with KG-1 cells as compared with HL-60 cells i.e., ~5 times, as indicated from frequency and resistance changes. As such, the biosensor is capable of differentiating between AML cells with varied abilities to adhere to activated ECs.

$R_1$ represents the energy dissipation of the quartz crystal resonance into the surrounding environment and the onset responses of $R_1$, in principle, can be understood from changes in density and viscosity of solution, the cell layer adsorbed onto the electrode surface, etc. The enhanced $\Delta R_1$ shifts in Stage III suggest that the binding of AML cells with HUVECs induced the increase of the cell layer density and viscosity on the electrode. Furthermore, the $|\Delta f_0/\Delta R_1|$ ratios after introduction of HL-60 cells and KG-1 cells were calculated to be 13 Hz Ω$^{-1}$ and 25 Hz Ω$^{-1}$. This means that the mass effect was a main factor controlling the QCM signal shift, i.e., the adhesion of AML cells on HUVECs could result in the mass change of the cell layer at the interface.

Figure 9A:
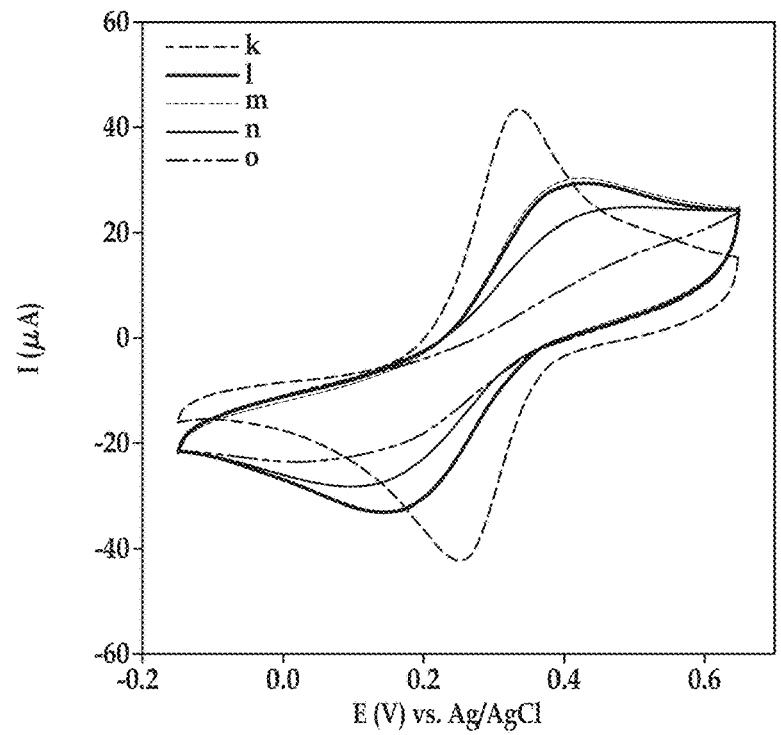
FIGS. 9A and 9B are Cyclic voltammograms (FIG. 9A) and electrochemical impedance spectra (FIG. 9B) of a bare QCM Au electrode (k), a QCM Au electrode modified with HUVECs (l), a QCM Au electrode modified with activated HUVECs (m), a QCM Au electrode modified with activated HUVECs and HL-60 cells (n) and a QCM Au electrode modified with activated HUVECs and KG-1 cells (o) in a pH 7.4 PBS containing 1 mM $K_3Fe(CN)_6$, 1 mM $K_4Fe(CN)_6$, and 0.2 M $KNO_3$.
Figure 9B:
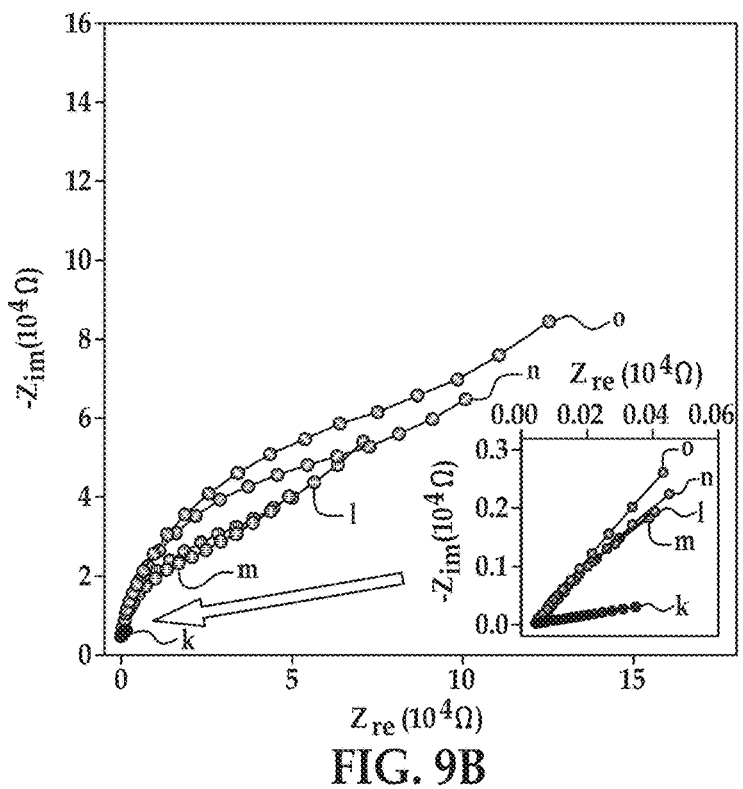
Figure 10A:
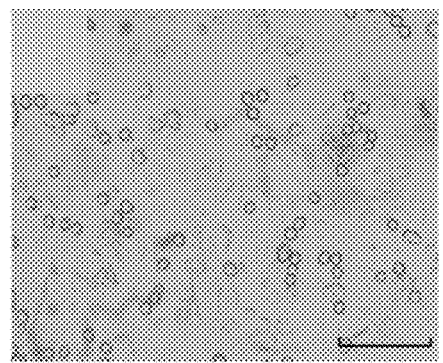
FIGS. 10A through 10D are microscope images of HL-60 cells (FIGS. 10A and 10C) and KG-1 cells (FIGS. 10B and 10D) adhered on HUVECs (FIGS. 10A and 10B) and pre-activated HUVECs (FIGS. 10C and 10D) using a 10× objective, the scale bar represents 50 µm.
Figure 10B:
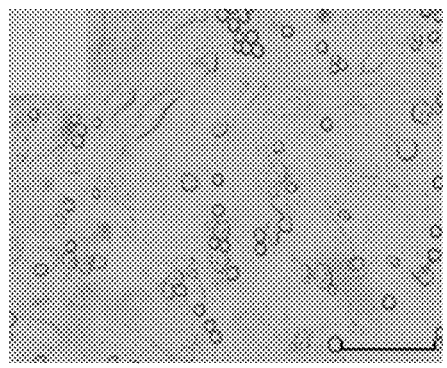
Figure 10C:
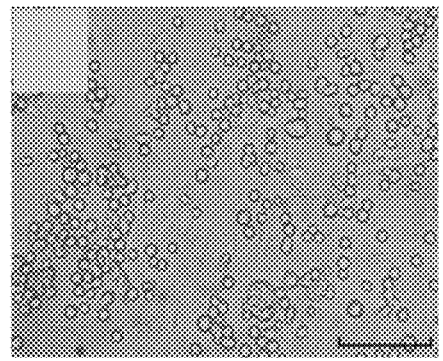
Figure 10D:
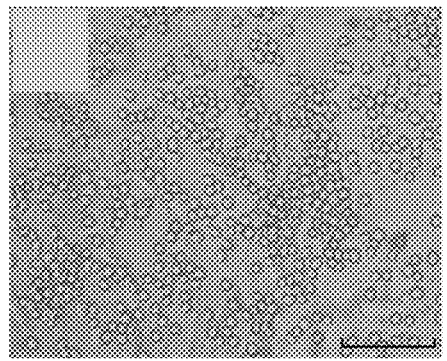

FIGS. 9A and 9B show the cyclic voltammograms (CV) and electrochemical impedance spectra (EIS) experimental results using the QCM gold electrodes modified with different cells. Sample k was the bare QCM Au electrode, sample l was the QCM Au electrode modified with HUVECs, sample m was the QCM Au electrode modified with activated HUVECs, sample n was the QCM Au electrode modified with activated HUVECs and HL-60 cells, and sample o was the QCM Au electrode modified with activated HUVECs and KG-1 cells. For cyclic voltammetry, the scan rate was 50 mV s$^{-1}$, and for the EIS experiment, the AC frequency range was 100 kHz~5 mHz, the amplitude was 10 mV, the DC bias was an open potential, and the reference electrode was saturated Ag/AgCl. As shown in FIG. 9A, the peak current responses were decreased with the increased peak to peak separation, and as shown in FIG. 9B, the Nyquist diameter was enhanced to a large extent after the immobilization of HUVECs. These results revealed that the adhered cells efficiently blocked the electron transfers of ferri-/ferrocyanide probe. It seems that the activation of HUVECs had little influence on the electrochemical properties of the cell modified electrode.

As shown in FIGS. 9A and 9B, the above-mentioned electrochemical parameters were further changed with the introduction of AML cells, proving that the leukemia cells were effectively captured by the activated ECs. The negative effect of KG-1 cells on the electron transfer was more obvious as the KG-1 cell-bound electrode (sample o) presented smaller peak current responses and larger electron transfer resistance than the HL-60 cell-bound electrode (sample n) did. This demonstrates that it was easier for KG-1 cells to be bound on the activated HUVECs. The KG-1 cells have a higher propensity to activate and adhere to HUVECs compared to HL-60s.

The microscope observation of the bound AML cells was performed and the results are shown in FIGS. 10A through 10D. Similar numbers of HL-60 (FIGS. 10A and 10C) and KG-1 cells (FIGS. 10B and 10D) were introduced onto resting HUVECs (FIGS. 10A and 10B and activated HUVECs (FIGS. 10C and 10D) in a 96 well plate. The number of initially planted HUVECs was $3\times10^4$ cells, the concentration of used TNF-α (for pre-activated HUVECs, FIGS. 10C and 10D) was 200 ng mL$^{-1}$, and the number of added leukemia cells was $25\times10^4$ cells. Twenty two hours later, wells were rinsed with PBS three times to remove non-adherent cells and were filled with EGM-2 medium. It was found that fewer AML cells adhered to resting HUVECs in comparison to the activated HUVECs (comparing FIGS. 10A and 10B to FIGS. 10C and 10D). In addition, the number of adherent KG-1 cells was larger than that of HL-60 cells (comparing FIGS. 10B and 10D to FIGS. 10A and 10C). These images indicate that the activation of HUVECs is an important factor leading to the binding of AML cells.

The expression of CAM receptors on KG-1 cells may be more dominant than that on HL-60 cells, which could explain the stronger adhesion for the KG-1 cells. The information revealed by the CV and EIS experiments, as well as the microscope observation are all in complete accordance with the QCM measurements.

Figure 11A:
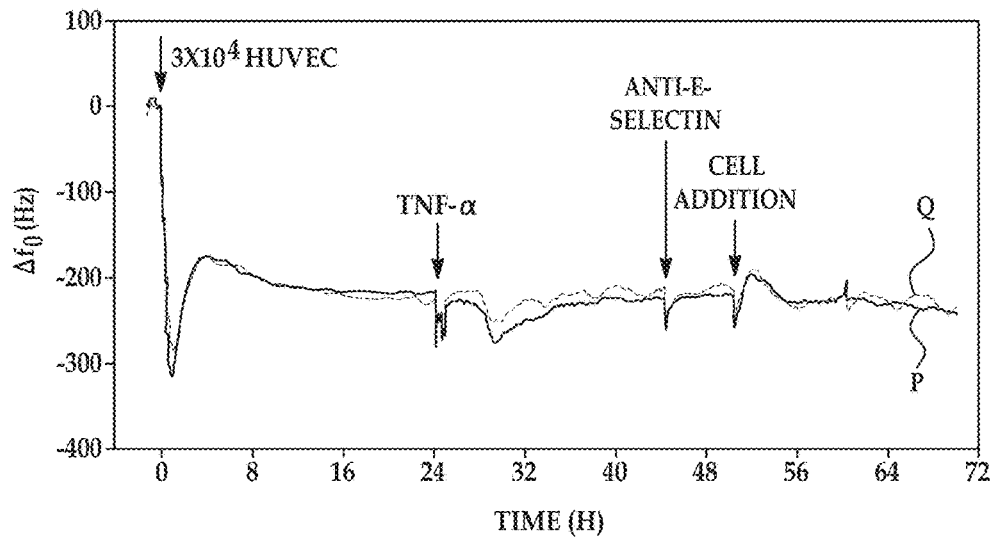
FIGS. 11A and 11B are plots depicting real-time $\Delta f_0$ (FIG. 11A) and $\Delta R_1$ (FIG. 11B) responses to the successive addition of $3 \times 10^4$ HUVECs, 200 ng mL$^{-1}$ TNF-$\alpha$, 1 mg mL$^{-1}$ anti-E-selectin, and $25 \times 10^4$ HL-60 cells (p) or $25 \times 10^4$ KG-1 cells (q) (24 hours later)
Figure 11B:
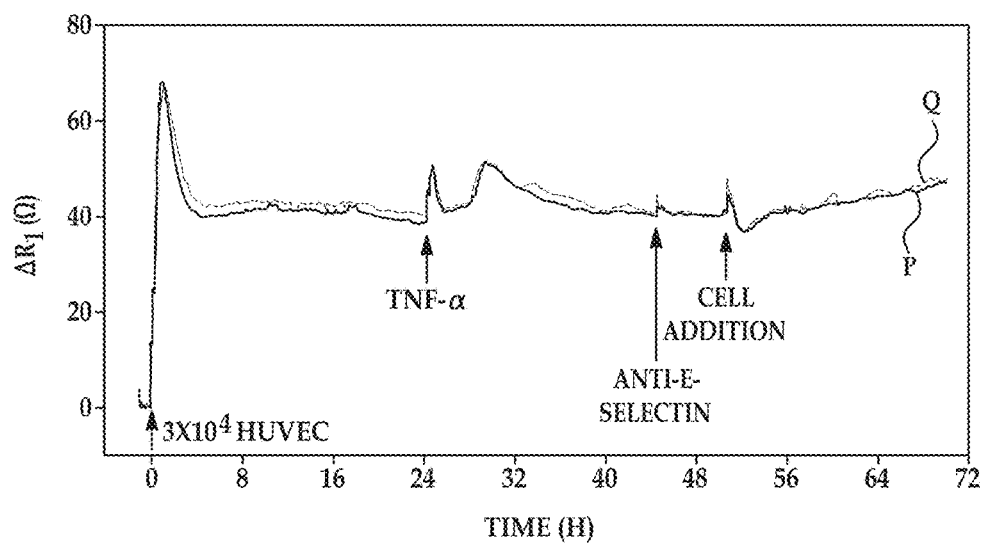

Indirect evidence of EC activation and the binding of the leukemia cells with only the activated cells came from a control experiment where 1 μg ml$^{-1}$ of anti-E-selectin antibody was added after the addition of 200 ng mL$^{-1}$ TNF-α into the measurement chamber and before the introduction of AML cells (i.e., $25\times10^4$ HL-60 cells (p in FIGS. 11A and 11B) and $25\times10^4$ KG-1 cells (q in FIGS. 11A and 11B)). These results are shown in FIGS. 11A and 11B. This experiment shows the reproducibility with the deviation calculated to be <10%. The activation by TNF-α caused very similar changes both in frequency and motional resistance to those observed in the previous experiments. However, the addition of anti-E selectin antibody could block E-selectin, thereby restricting the binding of the HL-60 and KG-1 cells even to the activated ECs. Here, the addition of anti-E-selectin antibody caused no change in frequency and resistance trend lines. It is likely that the binding of anti-E-selectin antibody on the activated EC cell surface is beyond the decay length of QCM shear wave. Further addition of leukemic cells produced no measurable signals when compared to the results shown in FIGS. 8A and 8B. This means that the activated ECs behaved in a manner more like the non-activated ones, as most of their binding sites had been blocked by the anti-E-selectin antibody.

Discrimination and Quantification of AML Cells

Figure 12A:
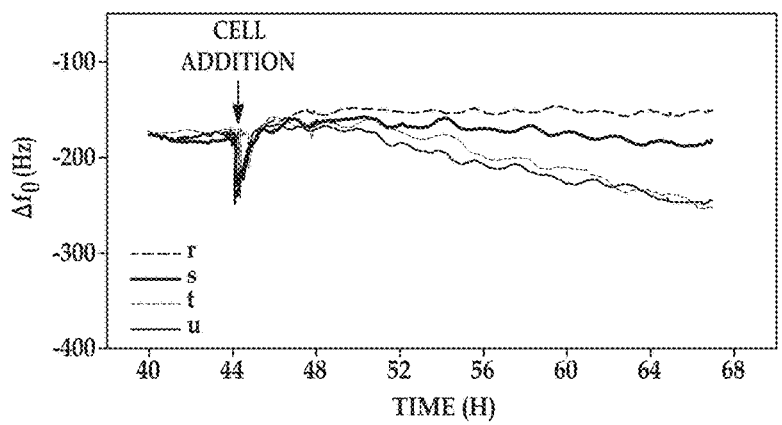
FIGS. 12A through 12D are plots depicting real-time $\Delta f_0$ (FIG. 12A) and $\Delta R_1$ (FIG. 12B) responses to the addition of $25 \times 10^4$ KG-1 cells on Au/activated HUVECs after activation by TNF-$\alpha$ with different concentrations; $|(\Delta f_0)|$ versus the concentration of TNF-$\alpha$ (i.e., $c_{TNF-\alpha}$) (FIG. 12C); and $\Delta R_1$ versus $c_{TNF-\alpha}$ (FIG. 12D); the results are presented as mean±SD (error bar) of triplicate experiments.
Figure 12B:
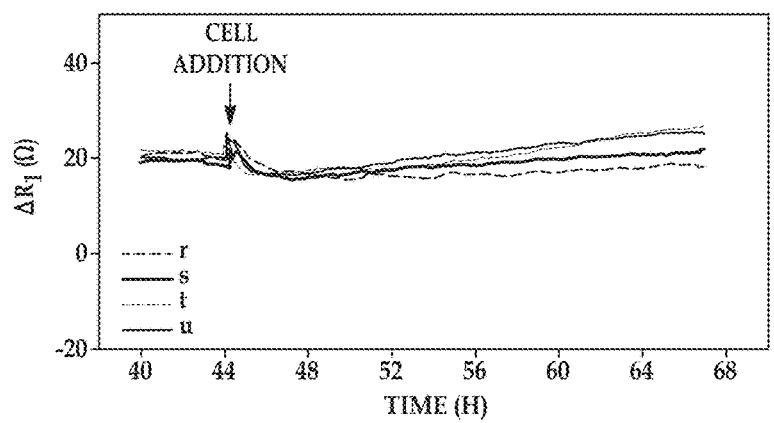
Figure 12C:
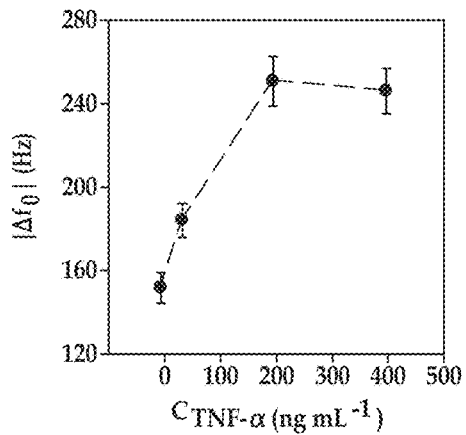
Figure 12D:
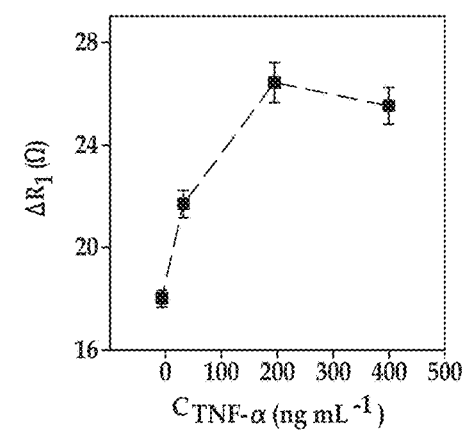

These examples confirmed that AML cells adhere to activated HUVECs based on binding with E-selectin. It is possible that the extent of activation of HUVECs, which is closely related to TNF-α concentration, should have an influence on the binding of AML cells. FIGS. 12A and 12B show the QCM responses induced by the addition of KG-1 cells with the same concentration (i.e., $25 \times 10^4$) on activated HUVECs after stimulation of TNF-α with different concentrations. For sample r, HUVEC activation was performed with 2 ng mL$^{-1}$ TNF-α; for sample s, HUVEC activation was performed with 40 ng mL$^{-1}$ TNF-α; for sample t, HUVEC activation was performed with 200 ng mL$^{-1}$ TNF-α; and for sample u, HUVEC activation was performed with 2 ng mL$^{-1}$ TNF-α. From FIGS. 12C and 12D, it was found that the QCM response shifts ($|\Delta f_0|$ and $\Delta R_1$ changes) were all increased with enhancement of TNF-α concentrations in the range of 2 ng mL$^{-1}$-200 ng mL$^{-1}$ and then suffered a slight decrease when the concentration of TNF-α was further increased. This data demonstrates that the extent of activation, promoted by TNF-α, directly correlates to the level of adhesion of KG-1 cells, and that this overall activity can be measured by the QCM sensor. The decreased QCM response shifts using TNF-α with higher concentrations, such as 400 ng mL$^{-1}$, might be related to the over activation and apoptosis of endothelial cells, which could have a negative effect on the adhesion of KG-1 cells. Based on these results, the concentration of TNF-α, 200 ng mL$^{-1}$, was selected for the next measurements.

FIGS. 13A1 and 13B1 show the $\Delta f_0$ shifts induced by the addition of different numbers of HL-60 and KG-1 cells on activated HUVECs, respectively. For samples v1 and v2, respectively, no (i.e., 0) HL-60 and KG-1 cells were added. For samples w1 and w2, respectively, $5 \times 10^4$ HL-60 and KG-1 cells were added. For samples x1 and x2, respectively, $10 \times 10^4$ HL-60 and KG-1 cells were added. For samples y1 and y2, respectively, $15 \times 10^4$ HL-60 and KG-1 cells were added. For samples z1 and z2, respectively, $25 \times 10^4$ HL-60 and KG-1 cells were added. For samples aa1 and aa2, respectively, $50 \times 10^4$ HL-60 and KG-1 cells were added. The frequency was clearly decreased with the introduction of AML cells, which was enhanced with the increasing number of suspension cells. In the presence of KG-1 cells, this shift was larger than that in the presence of HL-60 cells (comparing FIG. 13B1 with FIG. 13A1), indicating that both AML cells were successfully bound on the activated HUVECs, but that it was easier for the KG-1 cells to be captured.

FIGS. 13A2 and 13B2 show the relationship between $|(\Delta f_0)_n - (\Delta f_0)_0|$ and the number of HL-60 and KG-1 cells, respectively. The $|(\Delta f_0)_n - (\Delta f_0)_0|$ is defined as the decrease of $\Delta f_0$ signals, where $(\Delta f_0)_0$ and $(\Delta f_0)_n$ represent the frequency change in the absence $(\Delta f_0)_0$ and presence $(\Delta f_0)_n$ of AML cells, respectively. The value of $|(\Delta f_0)_n - (\Delta f_0)_0|$ represents the net frequency responses derived from the AML cell binding. It can be found that $|(\Delta f_0)_n - (\Delta f_0)_0|$ exhibited a linear response with respect to $N_{AML\ cells}$ over the range of the AML cell numbers from 0 to $25 \times 10^4$ cells. The regression equations were $|(\Delta f_0)_n - (\Delta f_0)_0| = 2.19 N_{cell}\ (\times 10^4) + 1.69$ for HL-60 cells and $|(\Delta f_0)_n - (\Delta f_0)_0| = 4.27 N_{cell}\ (\times 10^4) - 0.20$ for KG-1 cells, respectively, with a high correlation coefficient of 0.997. The above results indicate that the method demonstrated here provides a valid strategy for quantitative detection of adherent AML cells and for discrimination between two types of leukemia cells, i.e. HL-60 cells and KG-1 cells.

Conclusions

The attachment and growth of HUVECs, their activation by TNF-α and subsequent binding of HL-60 and KG-1 leukemia cell lines were studied on the QCM gold electrode. The results showed $\Delta f_0$ and $\Delta R_1$ shifts that can be related to mechanical energy changes of these cells via the models described herein. The activated HUVECs underwent expected cell-shape changes accompanied with decreased spreading area, leading to the decline of density and viscosity of cell layer on the electrode surface, which was revealed by the QCM, CV, EIS and microscopic measurements.

It was difficult for AML cells, which grow in suspension, to bind the gold electrode or resting HUVECs. However, these suspension cells could be effectively captured by activated HUVECs that could express sufficient CAMs after stimulation by TNF-α, presenting the decreased $\Delta f_0$ and increased $\Delta R_1$ shifts, which were mainly attributed to the mass effect. The sensitivity of the method validated its use for discrimination and quantification of different AML cells based on QCM responses. This study validates that QCM techniques can sensitively and quickly measure changes in cell activity particularly cell-cell interactions such as those inherent to EC activation and provides real time data in comparison to traditional techniques (e.g., flow cytometry and IHC assays).

Furthermore, the results disclosed herein suggest that EC activation can be used as a biomarker of AML disease states by detecting EC activation and leukemia cell adhesion on ECs by potentially using a small quantity of peripheral blood cells from patients. Additionally, this label free biosensor may be used in a variety of applications for real-time and non-invasive investigation on intercellular actions in vitro, which may lead to better understanding of patients' responses to chemotherapy.

By activating ECs with TNF-α and then characterizing their binding with HL-60 and KG-1 leukemia cells, the present inventors have found that it is possible to induce mechanical changes in ECs, especially in the region of cell-substrate contact. This resulted in dynamically coupled mass and viscoelastic changes, representing the extent of both activation and binding. The activated ECs suffered a decrease of cellular contact area, leading to positive frequency shift and decreased motional resistance. The binding of leukemia cells onto pre-activated ECs exerted a mechanical force to regain the cell surface contact which resulted in QCM responses opposite to that of activation, and proportional to the number of cells added, in spite of the fact that these added cells are extremely outside the extinction boundary of the shear wave generated by QCM.

It has been found that different cell lines demonstrate different attachment behavior, which can be detected by the QCM. Even when the variations are quite subtle, the sensitivity of the technique for dynamic changes at the interface makes the variations detectable. Moreover, the reproducibility of the generated data determined at each step by deviation measurements (<10%) in response plot is very high despite possible heterogeneity in cell populations.

Example 2

Figure 14:
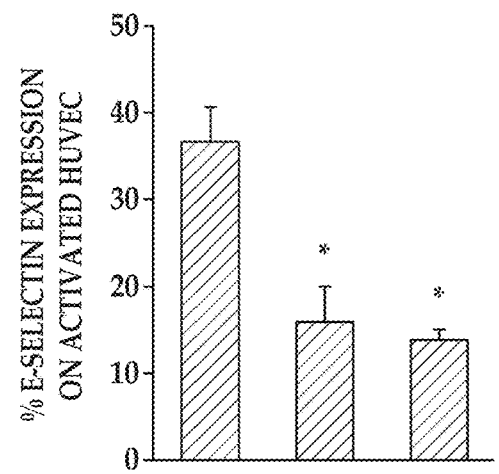
FIG. 14 is a graph depicting the percentage of E-selectin expression on activated HUVECs for a control sample, after the addition of Thalidomide, and after the addition of Lenalidomide.

As illustrated throughout Example 1, acute myeloid leukemia (AML) cells mediate endothelial cell (EC) activation. In this Example, the effects of anti-inflammatories, namely thalidomide and lenalidomide, to prevent AML induced EC activation were tested. KG-1 cells were pre-treated with 100 µM thalidomide or 1 µM lenalidomide (half of total dose) for 1-hour. Co-cultures were then established by adding the pre-treated KG-1 cells ($1 \times 10^6$ cells) to cultures containing HUVECs (~80% confluence) with the addition of the second half of the total dose of the respective anti-inflammatories. After 24-hours, E-selectin expression on HUVECs was measured as a marker of EC activation using flow cytometry. Untreated (i.e., no anti-inflammatory added) co-cultures of KG-1 on HUVECs were used as controls. The results are shown in FIG. 14, where the + indicates whether the co-culture was the control, was treated with thalidomide, or was treated with lenalidomide. The data in FIG. 14 shows that there was a significant reduction of E-selectin expression on HUVECs in co-cultures treated with either thalidomide or lenalidomide. These results indicate that both compounds were able to reduce EC activation.

Figure 15:
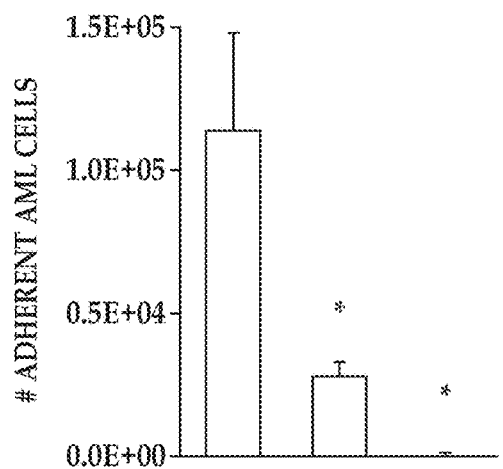
FIG. 15 is a graph depicting the number of adherent acute myelogenous leukemia cells (AML cells) on HUVECs for a control sample, after the addition of Thalidomide, and after the addition of Lenalidomide.

It was determined whether thalidomide and lenalidomide were able to reduce EC activation mediated AML cell adhesion. Adherent cells were collected from treated (as described above) and control co-cultures, and the numbers of adherent AML cells in each population were enumerated based on flow cytometric analysis. The results are shown in FIG. 15. These results demonstrate that thalidomide and lenalidomide were able to significantly reduce the numbers of adherent AML cells in comparison to untreated controls. Therefore, prevention of EC activation using these compounds was able to prevent AML cell adhesion and may provide a method to augment chemotherapy and eliminate adherent AML cells that play a role in relapse.

It is to be understood that the ranges provided herein include the stated range and any value or sub-range within the stated range. For example, a range from about 2 ng ml$^{-1}$ to about 200 ng ml$^{-1}$ should be interpreted to include not only the explicitly recited limits of about 2 ng ml$^{-1}$ to about 200 ng ml$^{-1}$, but also to include individual values, such as 25 ng ml$^{-1}$ to about 150 ng ml$^{-1}$, etc., and sub-ranges, such as from about 15 ng ml$^{-1}$ to about 180 ng ml$^{-1}$, from about 50.5 ng ml$^{-1}$ to about 100 ng ml$^{-1}$, etc. Furthermore, when "about" is utilized to describe a value, this is meant to encompass minor variations (up to +/−10%) from the stated value.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

In describing and claiming the examples disclosed herein, the singular forms "a", "an", and "the" include plural referents unless the context clearly dictates otherwise.

While several examples have been described in detail, it will be apparent that the disclosed examples may be modified. Therefore, the foregoing description is to be considered non-limiting.

What is claimed is:

1. A method for monitoring cell-to-cell interactions, the method comprising:
    exposing a surface of a quartz crystal microbalance to a medium including a first cell;
    exposing the first cell to a sample including a suspect cell;
    activating the first cell on the surface either prior to the exposing of the first cell to the sample or simultaneously with the exposing of the first cell to the sample;
    measuring a frequency change versus time and a motional resistance change versus time:
        after each of the exposing of the surface to the medium including the first cell, the activating that takes place prior to the exposing of the first cell to the sample, and the exposing of the first cell to the sample; or
        after each of the exposing of the surface to the medium including the first cell and the simultaneous activating and exposing; and
    from the frequency changes versus time and the motional resistance changes versus time, determining any of i) a level of adhesion of the suspect cell to the activated first cell, or ii) a type of the suspect cell, or iii) a behavior or activity of the suspect cell, or iv) activation of the first cell.

2. The method as defined in claim 1 wherein the activating is accomplished prior to the exposing of the first cell to the sample including the suspect cell, and wherein the activating includes exposing the first cell to a predetermined concentration of an activation agent.

3. The method as defined in claim 2, further comprising using the predetermined concentration in the determining step to determine the level of adhesion of the suspect cell to the activated first cell.

4. The method as defined in claim 1 wherein the activating is accomplished simultaneously with the exposing of the first cell to the sample including the suspect cell, and wherein the sample further includes an activation agent.

5. The method as defined in claim 1 wherein the first cell is a cell of a first type that is capable of interacting with the surface of the quartz crystal microbalance, and wherein the suspect cell is a cell of a second type that is capable of interacting with the activated first cell.

6. The method as defined in claim 5 wherein the first cell is an endothelial cell and the suspect cell is selected from the group consisting of a leukemia cell, a red blood cell, a white blood cell, and a platelet.

7. The method as defined in claim 1 wherein the method is performed without a label.

8. The method as defined in claim 1 wherein prior to the exposing of the surface of the quartz crystal microbalance to the medium including the first cell, the method further comprises:
    exposing the surface of the quartz crystal microbalance to a blank medium for a predetermined time;
    while the surface of the quartz crystal microbalance is exposed to the blank medium, measuring a change in frequency versus time and a change in motional resistance versus time; and
    identifying a resonant frequency baseline value and a motional resistance baseline value when the changes in frequency versus time and motional resistance versus time stabilize while the surface of the quartz crystal microbalance is exposed to the blank medium.

9. The method as defined in claim 8 wherein after the exposing of the surface of the surface of the quartz crystal microbalance to the medium including the first cell, the method further comprises:

performing a quality control step by:
 measuring the frequency change versus time and the motional resistance change versus time after the exposing of the surface to the medium including the first cell; and
 allowing a frequency change signal and a motional resistance change signal to return to the resonant frequency baseline value and the motional resistance baseline value, respectively, before exposing the first cell to the sample including the suspect cell.

10. The method as defined in claim 1, further comprising performing at least some of the measuring of the frequency changes versus time and motional resistance changes versus time in the presence of an agent that affects any of the level of adhesion of the suspect cell to the first cell or the behavior or activity of the suspect cell.

11. The method as defined in claim 10, further comprising exposing the first cell to the agent after each of the exposing of the surface to the medium including the first cell and the activating that takes place prior to the exposing of the first cell to the sample, but prior to the exposing of the first cell to the sample including the suspect cell.

12. The method as defined in claim 11 wherein a predetermined concentration of the agent is used.

13. The method as defined in claim 11 wherein the agent is a compound that can prevent the adhesion of the suspect cell to the first cell.

14. The method as defined in claim 13 wherein the agent is an antibody.

15. The method as defined in claim 10, further comprising exposing the first cell and the suspect cell to the agent:
 after each of the exposing of the surface to the medium including the first cell, the activating that takes place prior to the exposing of the first cell to the sample, and the exposing of the first cell to the sample; or
 after each of the exposing of the surface to the medium including the first cell and the simultaneous activating and exposing.

16. A method for monitoring cell-to-cell interactions, the method comprising:
 exposing a surface of a quartz crystal microbalance to a medium including a first cell;
 simultaneously exposing the first cell to an agent and a sample including a suspect cell, thereby attempting to activate the first cell;
 measuring a frequency change versus time and a motional resistance change versus time after each of the exposing of the surface to the medium including the first cell, and the simultaneous exposing; and
 from the frequency changes versus time and the motional resistance changes versus time, determining whether the agent prevents activation of the first cell.

17. The method as defined in claim 16 wherein the agent affects the activation of the first cell.

18. The method as defined in claim 16, further comprising incubating the sample including the suspect cell with the agent prior to simultaneously exposing the first cell to the agent and to the sample including the suspect cell.

* * * * *